(12) United States Patent
Bergman et al.

(10) Patent No.: US 7,977,529 B2
(45) Date of Patent: Jul. 12, 2011

(54) INCONTINENCE MANAGEMENT SYSTEM AND DIAPER

(75) Inventors: Frederick Bergman, Caulfield (AU); Ari Bergman, legal representative, Caulfield (AU); David Albert Barda, Docklands (AU); Daniel Weinstock, Caulfield South (AU); Remi Guibert, Mount Martha (AU); Maria C. Rodda, Mount Eliza (AU); Guy Eitzen, Wheelers Hill (AU)

(73) Assignee: Fred Bergman Healthcare Pty Ltd., Melbourne (AU)

( * ) Notice: Subject to any disclaimer, the term of this patent is extended or adjusted under 35 U.S.C. 154(b) by 823 days.

(21) Appl. No.: 11/797,352

(22) Filed: May 2, 2007

(65) Prior Publication Data
US 2007/0270774 A1 Nov. 22, 2007

Related U.S. Application Data

(63) Continuation-in-part of application No. PCT/AU2005/001667, filed on Oct. 28, 2005.

(30) Foreign Application Priority Data

Nov. 3, 2004 (AU) .............................. 2004906315
May 2, 2006 (AU) .............................. 2006902251

(51) Int. Cl.
*A61F 13/15* (2006.01)
*G06Q 10/00* (2006.01)

(52) U.S. Cl. .................. 604/361; 604/385.01; 702/177; 702/180; 702/181; 702/188; 702/189; 703/11; 703/16; 703/17; 705/2; 705/3

(58) Field of Classification Search .................. 604/361, 604/385.01; 702/177, 180, 181, 188, 189; 703/11, 16, 17; 705/2, 3
See application file for complete search history.

(56) References Cited

U.S. PATENT DOCUMENTS 4,356,818 A * 11/1982 Macias et al. ................. 128/886
4,507,121 A    3/1985 Leung
(Continued)

FOREIGN PATENT DOCUMENTS
CA    2 361 132    5/2002
(Continued)

OTHER PUBLICATIONS

Wu et al. "Odor-Based Incontinence Sensor." Robotics Institute, School of Computer Science, 2000, pp. 63-68.
(Continued)

*Primary Examiner* — Tatyana Zalukaeva
*Assistant Examiner* — Ginger T Chapman
(74) *Attorney, Agent, or Firm* — Jacobson Holman PLLC

(57) ABSTRACT

An incontinence management system for monitoring wetness in one or more absorbent articles, includes input for receiving one or more sensor signals indicative of a presence of wetness in an absorbent article, processor for processing the one or more sensor signals and for performing an analysis of the signals to characterise wetness events occurring in an absorbent article and user interface for communicating with a user of the system. A mathematical model is used to characterise wetness events, receiving as inputs variables derived from sensor signals and optionally, patient and demographic data. The mathematical model can be configured and/or re-configured utilising observation data obtained while monitoring a patient for wetness. A diaper for use with such as system is also disclosed.

61 Claims, 11 Drawing Sheets

U.S. PATENT DOCUMENTS

| | | | |
|---|---|---|---|
| 4,539,559 | A | 9/1985 | Kelly et al. |
| 4,977,906 | A | 12/1990 | Di Scipio |
| 5,036,859 | A | 8/1991 | Brown |
| 5,074,317 | A * | 12/1991 | Bondell et al. ............... 128/886 |
| 5,103,835 | A * | 4/1992 | Yamada et al. ............... 600/547 |
| 5,262,944 | A * | 11/1993 | Weisner et al. ............... 600/300 |
| 5,264,830 | A | 11/1993 | Kline et al. |
| 5,416,469 | A | 5/1995 | Colling |
| 5,537,095 | A | 7/1996 | Dick et al. |
| 5,557,263 | A | 9/1996 | Fisher et al. |
| 5,568,128 | A | 10/1996 | Nair |
| 5,570,082 | A | 10/1996 | Mahgerefteh et al. |
| 5,680,590 | A * | 10/1997 | Parti ................................. 703/2 |
| 5,760,694 | A | 6/1998 | Nissim et al. |
| 5,790,036 | A | 8/1998 | Fisher et al. |
| 5,838,240 | A | 11/1998 | Johnson |
| 5,902,296 | A | 5/1999 | Fluyeras |
| 5,959,535 | A | 9/1999 | Remsburg |
| 6,091,336 | A | 7/2000 | Zand et al. |
| 6,093,869 | A * | 7/2000 | Roe et al. ........................ 604/361 |
| 6,097,297 | A | 8/2000 | Fard |
| 6,149,636 | A | 11/2000 | Roe et al. |
| 6,175,752 | B1 * | 1/2001 | Say et al. ....................... 600/345 |
| 6,246,330 | B1 * | 6/2001 | Nielsen .......................... 340/604 |
| 6,292,102 | B1 | 9/2001 | Smith |
| 6,384,296 | B1 | 5/2002 | Roe et al. |
| 6,384,728 | B1 | 5/2002 | Kanor et al. |
| 6,433,695 | B1 | 8/2002 | Kai et al. |
| 6,544,200 | B1 | 4/2003 | Smith et al. |
| 6,559,772 | B2 | 5/2003 | Zand et al. |
| 6,573,837 | B2 | 6/2003 | Bluteau |
| 6,603,403 | B2 * | 8/2003 | Jeutter et al. .................. 340/604 |
| 6,774,800 | B2 | 8/2004 | Friedman et al. |
| 6,876,303 | B2 | 4/2005 | Reeder et al. |
| 6,916,968 | B2 | 7/2005 | Shapira et al. |
| 7,049,969 | B2 | 5/2006 | Tamai |
| 7,053,781 | B1 | 5/2006 | Haire et al. |
| 7,071,830 | B2 | 7/2006 | Sahlberg et al. |
| 7,141,715 | B2 | 11/2006 | Shapira |
| 7,176,344 | B2 | 2/2007 | Gustafson et al. |
| 7,221,279 | B2 | 5/2007 | Nielsen |
| 7,250,547 | B1 | 7/2007 | Hofmeister |
| 7,454,314 | B2 * | 11/2008 | Holland et al. ............... 702/182 |
| 7,693,697 | B2 * | 4/2010 | Westenskow et al. .......... 703/11 |
| 2002/0003478 | A1 | 1/2002 | Zhao et al. |
| 2003/0011479 | A1 * | 1/2003 | Bluteau ......................... 340/573.5 |
| 2003/0060789 | A1 | 3/2003 | Shapira et al. |
| 2004/0100763 | A1 * | 5/2004 | Yuan et al. ..................... 361/685 |
| 2004/0220538 | A1 * | 11/2004 | Panopoulos .................. 604/361 |
| 2005/0033250 | A1 * | 2/2005 | Collette et al. ................. 604/361 |
| 2005/0043894 | A1 * | 2/2005 | Fernandez ...................... 702/19 |
| 2005/0046578 | A1 * | 3/2005 | Pires .......................... 340/573.5 |
| 2005/0131663 | A1 * | 6/2005 | Bangs et al. ..................... 703/11 |
| 2005/0156744 | A1 | 7/2005 | Pires |
| 2006/0139165 | A1 | 6/2006 | Bader |
| 2006/0253296 | A1 * | 11/2006 | Liisberg et al. .................. 705/1 |
| 2007/0288414 | A1 * | 12/2007 | Barajas et al. .................. 706/46 |

FOREIGN PATENT DOCUMENTS

| | | |
|---|---|---|
| DE | 198 37 678 | 3/2000 |
| EP | 1 047 033 | 10/2000 |
| EP | 1 063 624 | 12/2000 |
| EP | 1 567 998 | 8/2005 |
| FR | 2 733 146 | 10/1996 |
| WO | WO 96/14813 * | 5/1996 |
| WO | WO 97/42613 | 11/1997 |
| WO | WO 02/101679 | 12/2002 |
| WO | WO 2004/034929 | 4/2004 |
| WO | WO 2004/049969 | 6/2004 |
| WO | WO 2004/100763 | 11/2004 |
| WO | WO 2005/107580 | 11/2005 |
| WO | WO 2006/047815 | 5/2006 |

OTHER PUBLICATIONS

"Wet-Sense Monitoring System." Technology for Long Term Care. Feb. 19. 2006. www.techforltc.org/ltc.cfm?pageid=157&product=820&careissue=3.

"SenseSoft." Sensible Solutions. www.sensiblesolutions.se/index.php?option=com_content&task=view&id=25<emid=36.

"Incontinence event data logger." Date Logger. Jul. 8, 2000. www.medphys.ucl.ac.uk/udlh-compinst/instrumentation/past/data%20logger.htm.

"Roke Manor Research Develops Wireless Patient Monitor." Roker Manor Research Limited. Apr. 30, 2003. www.roke.co.uk/press/index.php?id=53&format=print.

"What Makes the Stay-Dri Continence Management System a System?" The Stay-Dri System. www.staydrisystem.com/home/frames/system.asp.

"Compare and Review Bed Wetting Alarms." www.enuresisalarms.com/bed-waiting-alarm-reviews-comparison-chart.htm.

"Sensatec® Care 3." Technology for Long Term Care. Jul. 16, 2007. www.techforltc.org/ltc.cfm?pageid=157&product=764&careetissue=3.

"Wireless Alarm & Record Wetness Sensor and Toilet Trainer." Malem Medical. www.malem.co.uk/Expand.asp?ProductCode=MO7.

* cited by examiner

INCONTINENCE MANAGEMENT SYSTEM AND DIAPER

This is a Continuation-in-Part of PCT/AU2005/001667 filed 28 Oct. 2007 and published in English.

FIELD OF THE INVENTION

The present invention relates to moisture monitoring. It relates particularly but not exclusively to systems, devices and methods for monitoring moisture in absorbent articles such as diapers, incontinence garments, dressings and pads, resulting from wetness events caused by, for example, urinary and/or faecal incontinence. It also relates to a diaper for use with such a system.

BACKGROUND OF THE INVENTION

Incontinence is a condition in which there is uncontrolled release of natural discharges or evacuations. While some forms of incontinence are more widespread, the condition usually affects women, the elderly and the infirm. Urinary incontinence refers to loss of bladder control resulting in involuntary or uncontrolled urination. Other forms of incontinence including faecal or bowel incontinence also exist. In the context of the present application, the term "incontinence" is to be taken to include urinary and faecal incontinence.

Incontinence, in the context of this specification, includes urinary and faecal incontinence, and management of such incontinence is to be seen in the context of persons located in hospitals, nursing homes, aged care facilities, geriatric institutions, private homes and the like.

The aforementioned incontinence, when unchecked, may result in the person suffering from the condition experiencing discomfort or at least embarrassment, and in the existence of unpleasant odours and environment for others in the vicinity of the person. In addition, health regulations or protocols may prescribe a maximum period, such as 15 minutes, for which a patient may be left in a wet state caused by incontinence. In the past, to comply with such requirements, it has been necessary for nursing staff to manually check each patient at least once during the prescribed period. Apart from the unpleasantness experienced by nursing staff in carrying out such manual checks, such a regimen may place a severe strain on staff resources, and may constitute an interruption to patients' rest and sleep.

A range of different incontinence types are recognised. Stress incontinence refers to involuntary loss of urine immediately associated with coughing, sneezing, lifting, straining or other physical exertion. The term "stress" relates to the mechanical stress of the abdominal muscles compressing the bladder wall, working against weakened sphincter muscles. Childbirth, obesity, constipation and changes in the sphincter muscles after the menopause can aggravate stress incontinence as can the use of some drugs.

Urge incontinence refers to the involuntary loss of urine coupled with a strong desire to urinate. Often the sufferer is unable to reach the toilet before there has been a urine loss. The need to visit the toilet may occur very frequently during the day and often at night also. Urge incontinence is generally caused by an overactive or "unstable" bladder which contracts involuntarily in an attempt to empty. The contractions give rise to an urgent desire to pass urine and uncontrolled leakage occurs before a toilet is reached. Mixed Urinary Incontinence (MUI) refers to involuntary leakage associated with urge incontinence and also with exertion, effort, sneezing, or coughing associated with stress incontinence.

Overflow incontinence refers to involuntary loss of urine associated with a chronically distended and overfull bladder. The bladder may be distended as a result of incomplete emptying which may be caused by obstruction to the outlet of the bladder or as a result of a failure of the bladder muscle to contract properly. Bladder failure of this kind may be caused by disease of the nervous system, by some drugs or by psychological factors.

Dribble incontinence refers to leakage of urine without warning or provocation. This is a demoralising condition because leakage can occur at anytime and is unpredictable. Persons suffering from dribble incontinence often need to wear protective pads or diapers throughout the day and night. Total incontinence is a term sometimes used to describe continuous leaking of urine, day and night, or periodic large volumes of urine and uncontrollable leaking. Some people have this type of incontinence because they were born with an anatomical defect. It can also be caused by a spinal cord injury or by injury to the urinary system from surgery.

Functional incontinence occurs where the ability to get to the toilet is impaired either by physical conditions such as paralysis or arthritis, or mental impairment. This is very common in nursing home patients who rely on assistance from others for mobility.

Although incontinence is relatively widespread, it is a condition which must be treated with sensitivity as it can be uncomfortable and embarrassing for sufferers and carers alike. When left unchecked, incontinence can become more embarrassing due to the existence of unpleasant odours associated with incontinence events and this can create an unpleasant environment for others in the vicinity of the incontinence sufferer. In addition, exudate escaping the body as the result of an incontinence event often contains bacteria, so unchecked wetness can create health and hygiene problems. Also, health regulations or protocols may prescribe a maximum period, for example 15 minutes, for which a patient suffering incontinence may be left in a wet state.

In the past, to comply with regulations and protocols and to ensure that patients in care institutions such as hospitals, nursing homes, aged care facilities and geriatric institutions are well looked after, it has been necessary for staff to manually check patients suffering from incontinence on a regular basis. Apart from the unpleasantness involved with manual checks, such a regimen also places a strain on staff resources. Often manually checking for wetness will also cause interruption to a patient's rest and sleep.

Incontinence indicators and detection systems exist. However, they have done little to improve the current situation in which carers must manually and regularly check patients for wetness. Existing incontinence detection systems are generally unable to distinguish a urinary incontinence event from a fecal incontinence event or the size of these events. Existing systems are also deficient in that they alarm or alert a carer simply when wetness is detected, with no indication of the degree of wetness present. This can cause more time wasted than saved as very small volumes e.g. of urine or perspiration may trigger an alert even though the patient does not actually require attention from a carer. This can also be a source of embarrassment for the patient.

Some systems involve complicated circuitry and are expensive and difficult to manufacture. Since most diapers and pads are disposable both for efficiency of use and hygiene reasons, complicated sensor systems do not lend themselves to widespread uptake and ongoing use.

Some systems are clumsy to use and the sensors can interfere with the absorbent capacity of the diaper or pad with which they are used. Others again are generally incompatible with current care practices and actually create additional work, significant complications or changes in care practices undermining any benefits they may offer and making them less susceptible to widespread uptake and ongoing use.

The present invention aims to improve upon these systems, to improve efficiency in monitoring and management of continence with minimal changes in care practices, or at least provide a useful alternative to existing systems.

SUMMARY OF THE INVENTION

According to a first aspect of the present invention, there is provided a moisture monitoring system for monitoring wetness in one or more absorbent articles. The system includes an input for receiving one or more sensor signals indicative of a presence of wetness in an absorbent article, a processor for processing the one or more sensor signals and for performing an analysis of the signals to characterise wetness events occurring in an absorbent article and a user interface for communicating with a user of the system.

The processor may execute an algorithm to devise automatically a mathematical model for characterising a wetness event in an absorbent article. Alternatively, the processor executes an algorithm to perform the analysis, where the algorithm applies the sensor signals to a pre-determined mathematical model to characterise a wetness event in an absorbent article by determining e.g. an estimated volume of exudate in a wetness event and/or the nature of exudate in a wetness event. Alternatively the algorithm may apply variables derived from the one or more sensor signals to the mathematical model.

The processor may apply sensor signals and/or derive variables from the sensor signals for use by the algorithm to determine one or more parameters suitable for use in a mathematical model for characterising a wetness event. The sensor signals may indicate one or more of conductivity of the exudate, temperature of the exudate, location of the exudate, pH of the exudate, pressure within the absorbent article, odour within the absorbent article, presence of a gas in the absorbent article and presence of blood and/or a biological marker and/or a or chemical marker in the exudate.

Variables derived from the sensor signals may be selected from the group including but not limited to area under a sensor signal curve, highest sensor signal value in a predetermined time period, maximum value of a leading edge of the sensor signal, rate of decay of sensor signal after a leading edge, a volume estimated in a previous wetness event, time of onset of a wetness event, time of termination of a wetness event, duration of a wetness event, time of day of a wetness event and time elapsed since last wetness event.

The processor is configured to determine a range of predictions based on patterns identified from sensor signals and/or using mathematical models. These predictions may include a likelihood of an imminent wetness event, an estimate of when a wetness event is likely to occur, an estimate of a degree of fullness of an absorbent article and/or an estimate of when an absorbent article is likely to reach its absorbent capacity.

Preferably, the user interface includes a wireless transmitter configured to transmit a signal to a user of the system to indicate that a predetermined volume of wetness has been detected in an absorbent article. The processor may also be configured to provide a toileting or voiding diary and/or to derive a toileting or voiding schedule for an individual, based on wetness events monitored using the monitoring system, preferably over a number of days.

The system may predict, based on a derived toileting or voiding schedule, when an individual is likely to experience a wetness event which meets pre-defined criteria for manual checking. Further, the system may be adapted to communicate automatically, an alert to a carer when one or more pre-defined criteria for manual checking are satisfied.

In one embodiment, the processor is configured to classify a possible form of incontinence suffered by a patient monitored by the system, such as urinary, fecal, dribble, stress, overflow, urge, mixed urinary (MUI), total and functional incontinence. The processor may also recognise and/or predict lingering wetness in a region of an absorbent article.

The processor may be affixable to a sensor, an absorbent article or to a garment worn by a wearer of an absorbent article. Alternatively, the processor can be incorporated into a central monitoring station adapted to receive sensor signals from a plurality of sensors associated with one or more absorbent articles. A pre-processor may also be associated with a sensor of an absorbent article, locally to the article.

Preferably, the processor is adapted to execute an algorithm to reconfigure one or more mathematical models for use with one or more of a particular individual being monitored, a different sensor type and a different absorbent article type. This may be achieved by, for a training period using the particular individual, the different sensor type or the different absorbent article type, monitoring wetness at regular intervals by obtaining sensor signals and obtaining observation data, and reconfiguring the mathematical model so that there is satisfactory correlation between the estimates produced using the sensor signals and the reconfigured mathematical model, and the observation data obtained during the training period. Reconfiguring a mathematical model preferably involves employing an algorithm to determine one or more new parameters for the mathematical model e.g. using a linear regression technique.

Observation data includes measurements indicating an amount of wetness in the absorbent article and time of measurement. It may also include demographic information about the patient such as age and gender and patient information such as food and fluid intake and medication regimes.

According to another aspect of the present invention, there is provided a sensor for use with an absorbent article being monitored for wetness. The sensor includes a plurality of sensor elements arranged in a pattern which provides an improved ability to detect wetness. The pattern may involve more sensor elements in regions having higher propensity for variable moisture or temperature, within the absorbent article. The pattern may include sensor elements positioned toward the sides of the absorbent article, near an opening for receiving a leg of the wearer. The pattern may also include sensor elements located at two or more depths of the absorbent article. The sensor pattern includes one or more of elongate sensor elements, sensor elements arranged in a grid and an array of sensor element dots.

In one embodiment, one or more sensor elements extend beyond an edge of the absorbent article, preferably a front edge, and includes a connector for connecting the sensor elements to a signal receiver unit easily without significant disturbance to the patient being monitored.

A cover layer may be provided over the sensor elements which also extends beyond an edge of the absorbent article and includes means such as a pouch, pocket or flap for enclosing a signal receiver unit attachable to one or more of the sensor elements. It is preferable that one or more sensor elements are arranged for connection to a signal receiver unit outside the absorbent article.

The signal receiver unit may include storage means for storing sensor signals collected over a period of time. Alternatively or additionally, the signal receiver unit may include means for receiving data relating to a patient's toileting activities e.g. by way of buttons on the device, cable input or contactless communication. The signal receiver unit may also include a transmitter for transmitting sensor signals or variables derived therefrom to a remotely located device.

In one embodiment, the sensor includes a sensor substrate having one or more channels arranged between adjacent sensor elements. Such a sensor is suitable for use with an absorbent article having super absorbent material arranged correspondingly in the article, so as to draw fluid from the one or more channels in the sensor substrate. Preferably, the sensor is provided on a flexible substrate affixable, by adhesive or other means, to an absorbent article wearable by a user.

The sensor elements detect wetness at various identifiable locations with respect to the absorbent article including toward the front of the absorbent article, toward the rear of the absorbent article, toward a side of the absorbent article, and substantially centrally of the absorbent article. Desirably, the pattern of sensor elements facilitates improved detection of moisture from a user in a range of positions including standing, sitting, lying prone, lying supine and lying on the side. Preferably, the sensor elements are also arranged to detect spread of moisture from a wetness event in two or more directions. The sensor may include sensor elements for detecting one or more of electrical conductivity, temperature, pressure, pH, odour, gas and presence of a biological or chemical marker in exudate and location of exudate.

According to another aspect of the present invention, there is provided a method for monitoring moisture in an absorbent article including the steps of receiving one or more sensor signals associated with the absorbent article, the sensor signals indicating wetness in the absorbent article, applying one or more sensor signals to a predetermined mathematical model for characterising a wetness event and, based on the mathematical model, characterising a wetness event in the absorbent article. A method for devising the mathematical model is also disclosed.

Characterising a wetness event preferably involves ascertaining one or more of an estimated volume of exudate in a wetness event and the nature of the exudate although it may also involve determining whether predefined criteria, defined by a mathematical model, have been met. A user may be notified automatically if one or more predetermined notification criteria are met.

Preferably, the algorithm executing the predetermined mathematical model receives as inputs one or more variables derived from the one or more sensor signals and these variables may be derived automatically using a processor as described above. The method may also include maintaining a toileting or voiding diary, being a log of monitored wetness events, also referred to as a bladder chart. A toileting or voiding schedule may also be derived for an individual being monitored, based on wetness events monitored using the monitoring system.

The method may also include predicting, based on a derived toileting or voiding schedule, when an individual is likely experience a wetness event which meets pre-defined criteria for manual checking and this can streamline patient care. The method also facilitates reconfiguring of one or more mathematical models for use with one or more of a particular individual being monitored, a different sensor type and a different absorbent article type by, for a training period using the particular individual, the different sensor type and/or the different absorbent article type, monitoring wetness at regular intervals by obtaining sensor signals and obtaining observation data and reconfiguring the mathematical model so that there is satisfactory correlation between the estimates produced using the sensor signals and the reconfigured mathematical model, and the observation data obtained during the training period. Reconfiguring a mathematical model may involve determining new parameters for the mathematical model e.g. by application of a linear regression algorithm.

Another aspect of the present invention provides a diaper for a person to wear, for use in an incontinence management system or a system for the management of exudates from the body of a person, characterised in that said diaper includes a sleeve for the insertion of a diagnostic strip.

In another aspect of the present invention, there is provided a diaper for a person to wear, for use in an incontinence management system or a system for the management of exudates from the body of a person, characterised in that said diaper is provided with a plurality of sensors at different locations in said diaper.

In yet another embodiment of the invention, there is provided an incontinence management system or a system for the management of other exudates from the body of a person, characterised by an article adapted to be worn by the person, sensing means associated with said article and adapted to sense a condition, and transmitting means adapted to transmit a signal generated by said sensing means to a location.

BRIEF DESCRIPTION OF THE DRAWINGS

The present invention will now be described in greater detail with reference to the accompanying drawings. It is to be understood that the particularity of the accompanying drawings does not supersede the generality of the preceding description of the invention.

DETAILED DESCRIPTION

In one aspect, the present invention provides a system for monitoring wetness in one or more absorbent articles such as pads, diapers, adult incontinence garments or the like. Throughout this description, reference will be made to a range of absorbent articles. It is to be understood that the list of absorbent articles identified above is not an exhaustive list and that other absorbent articles and garments are within the scope of the present invention. It is also to be understood that a reference in this specification to any one such article, such as a "diaper" is to be taken to be a reference to any and all other suitable absorbent articles including incontinence garments, pads and the like.

The moisture monitoring system of the invention is generally intended for use in facilities in which staff are required to monitor and care for individuals who suffer from various incontinence conditions. These facilities include hospitals, nursing homes, aged care facilities, geriatric institutions, private homes, respite centres and the like, although it may also be used in other environments e.g. with infants. The system provides useful information to assist users, e.g. carers in the provision of more efficient care to sufferers of incontinence and the like.

As well as the urinary and faecal incontinence and wetness events referred to above, the present invention also has applicability in the detection, monitoring and management of conditions in which other fluids and exudates from the body may be present, including wound management. Thus, as well as the urinary and faecal incontinence, the present invention may be utilised in the management, monitoring and treatment of the production of other bodily fluids and exudates from the body of a patient or resident such as cerebro-spinal fluid (CSF), peritoneal fluid, synovial fluid from joints and bursae around joints, and material discharged from wounds.

Figure 1:
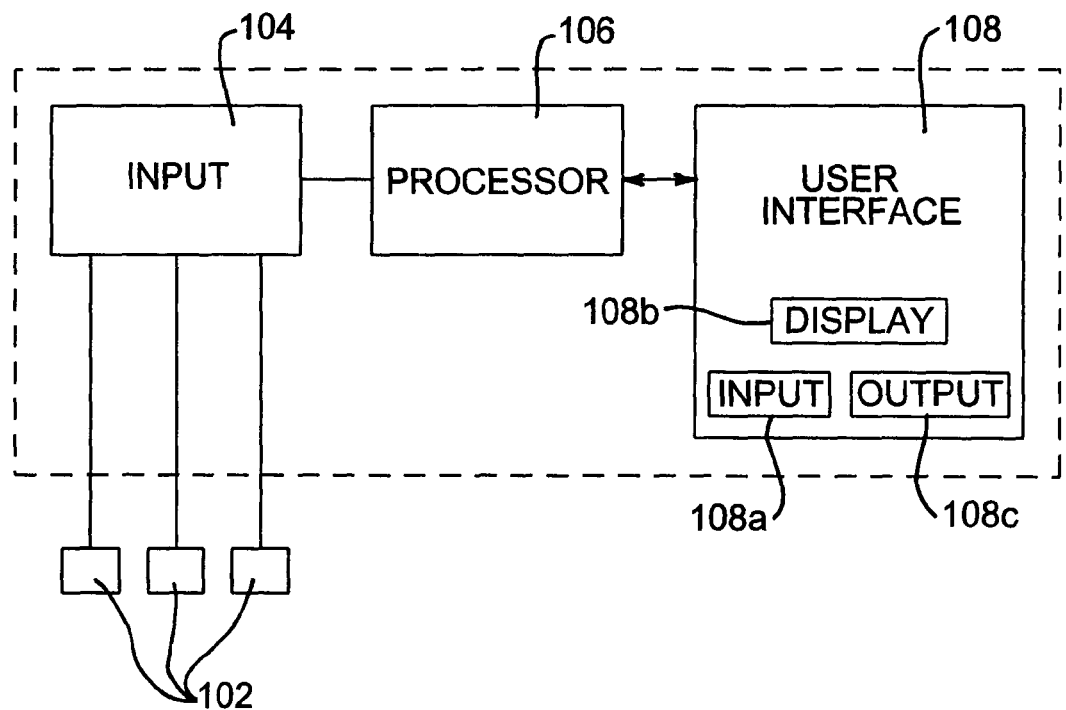
FIG. 1 is a schematic diagram illustrating features of a moisture monitoring system according to an embodiment of the present invention.

Referring now to FIG. 1 there is shown a schematic diagram illustrating features of a moisture monitoring system. The system includes input 104 which receives sensor signals, processor 106 and user interface 108. The system may be used with a plurality of sensors 102 each of which may be associated with a different individual being monitored. The sensor signals received by the input indicate whether moisture is present in an absorbent article being monitored. This may be achieved using a range of different sensor types and arrangements.

In one embodiment, presence of moisture is indicated by an increase in conductivity between spaced electrodes as a result of moisture forming a conductive bridge between them. These sensors could be replaced by or complemented with e.g. thermistor elements in which a change in temperature is indicative of the presence (or absence) of moisture. Conductivity and temperature signals will change with time, as moisture is drawn away from the skin's surface and into the absorbent article.

Alternatively or additionally, the sensor may include sensor elements monitoring other variables which change in the presence or absence of moisture (exudate), or when the volume of exudate changes. These sensor elements may include elements detecting changes in pH, pressure, odour and the presence of gas, blood, a chemical marker or a biological marker in the exudate, or any combination of these. The sensor elements may also be arranged in such a way that they convey to the processor the location of moisture detected.

An extensive list of clinically relevant medical conditions may be recognised or suspected by the detection of a number of metabolites, chemicals and ions, as well as other substances and cells of different types, in urine. Such materials as nitrites, amino acids, Beta-2 microglobulin, such measurements as pH, osmolality, white cell count, protein, specific gravity, and such conditions as multiple myeloma and haematuria, may be detected by testing urine from a patient e.g. using a sensor according to an embodiment of the invention.

Processor 106 executes an algorithm to perform an analysis of the sensor signals to characterise wetness events occurring in the absorbent articles being monitored. In one embodiment, the analysis involves modelling a relationship between a dependent variable such as volume of exudate in a wetness event, and sensor signals that can be used to estimate the volume. In one embodiment, the processor executes an algorithm to perform the analysis. Preferably, the algorithm applies variables derived from the sensor signals to the mathematical model to characterise a wetness event.

The algorithm may be programmed in software or in hardware using a range of different techniques and languages known to a person skilled in the relevant art. Advantageously, the algorithm enables the processor to combine different types of data which can be obtained from the sensor signals, and analyse that data to characterise a wetness event, thereby providing more useful information to a user of the system. Moreover, the algorithm enables the system to adapt to new sensor types and new types of absorbent article which have not been used with the moisture monitoring system before.

The processor may be configured to receive data (either entered manually or automatically by, for example, scanning a barcode on a diaper) pertaining to known features of a diaper or incontinence garment being worn by a patient. The features may include the volume, type or brand of the diaper/garment, and the location of the sensors embedded therein. This data enables the processor to identify the type of pad and devise or apply a suitable mathematical model which when used in combination with the data received from the sensor(s) can enable the processor to perform powerful analysis. Because the processor uses wetness and e.g. location data sampled over successive periods; and algorithms using mathematical models to characterise wetness events, it is also able to characterise phantom events or noise, which may result from the patient moving or from intermittent brief interference from other components in the system, and disregard these artefact points.

To characterise the volume of an event, the algorithm applies one or more variables derived from the sensor signals of an individual's absorbent article to a mathematical model which estimates the volume of liquid in the event. The variables derived from the sensor signals may include one or more of: area under a sensor signal curve (e.g. signal magnitude versus time); highest sensor signal value in a predetermined time period; maximum value of a leading edge of the sensor signal; the rate of decay of sensor signal after a leading edge; volume estimated in a previous event; time of onset; time of termination of an event; duration; time of day; and time elapsed since the last detected wetness event; although it is to be understood that this list is not exhaustive.

In addition to volume (or instead of), the algorithm may be adapted to characterise other aspects of wetness events such as the nature of the exudate (i.e. urinary or fecal) and whether a series of wetness events can be classified into a particular type of incontinence such as stress, urge, fecal, overflow, mixed urinary (MUI), dribble, functional and total incontinence. This can be achieved by applying a suitable mathematical model developed by the same means as the models used to characterise different voiding volumes.

Figure 4:
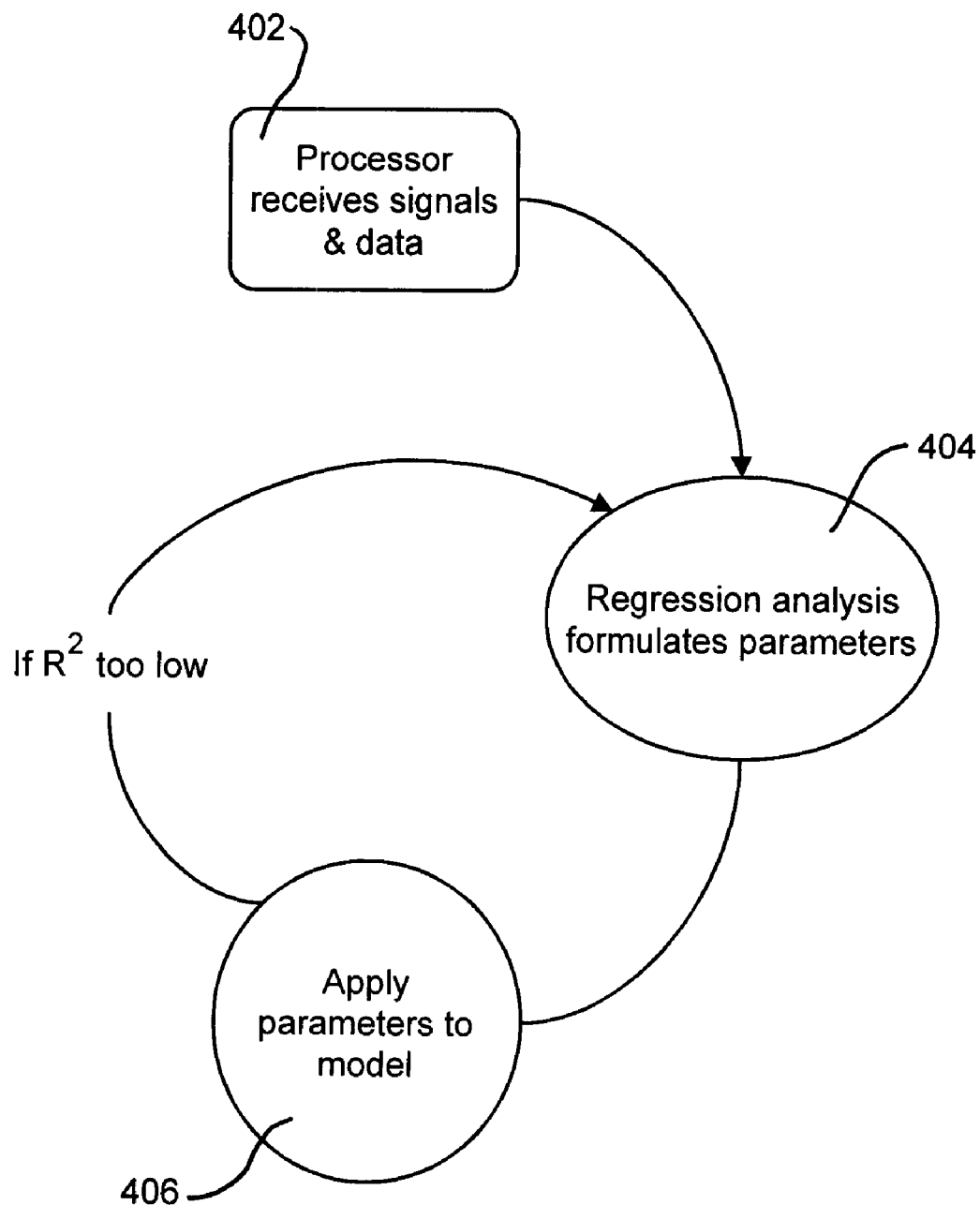
FIG. 4 is a flow diagram indicating the steps involved with calculating or re-calculating parameters of a mathematical model.

Referring now to FIG. 4, there is shown a flow diagram indicating steps involved in an algorithm calculating and/or recalculating parameters of a mathematical model to characterise wetness events with maximum accuracy and/or to optimise its performance.

For a training period, e.g. 3 days, a patient is monitored for wetness. This may involve continually monitoring sensor signals for indications of wetness and upon every variation in sensor values, obtaining observation data by changing the pad, examining the pad and weighing the pad. Additional observation data may be collected such as amount and time of fluid and food intake, as these variables influence the patient's continence function and are therefore potentially influential variables in the mathematical model.

In a step 402, the collected sensor signals and observation data are received by the processor. In a step 404, the processor executes an algorithm performing a regression analysis to formulate parameters for the mathematical model. In a step 406, these parameters are fed back into the mathematical model and a confidence level is determined which indicates how accurately the mathematical model estimates the actual events defined by the observation data. If the confidence level is acceptable (e.g. above $R^2$-0.6) then the parameters are accepted and the model updated. If the confidence level is too low, a further regression analysis is performed and the confidence level checked again. The algorithm repeats the regression analysis process until an acceptable confidence level is reached.

The same method may be applied to re-calculate parameters of the model. Calculating and recalculating the parameters of the mathematical model utilised by the system is useful for a number of reasons. Firstly, it enables the establishment of an initial mathematical model for predicting particular types of events. Secondly, it allows the system to continually improve the accuracy with which it predicts a patient's continence function and therefore, the efficiency with which care practices can be implemented. Thirdly, by reconfiguring the mathematical model, the system can be adapted to work with different absorbent pads having different absorbent characteristics. In this way, the algorithm can "learn" the characteristics of the pad.

Similarly, the system can adapt to use with additional and/or different sensor types. Again, the ability of the system to "learn" the behaviour of different sensors and sensor elements makes the system adaptable to new products and technologies which will improve accuracy and sensitivity, without the need for a major overhaul of the software employed by the processor. Alternatively/additionally, the processor may re-define one or more mathematical models to suit new sensors, sensor elements or absorbent articles. The need to re-define a mathematical model can be minimised by use of relatively generic code, although this can result in slower calculations.

Figure 2:
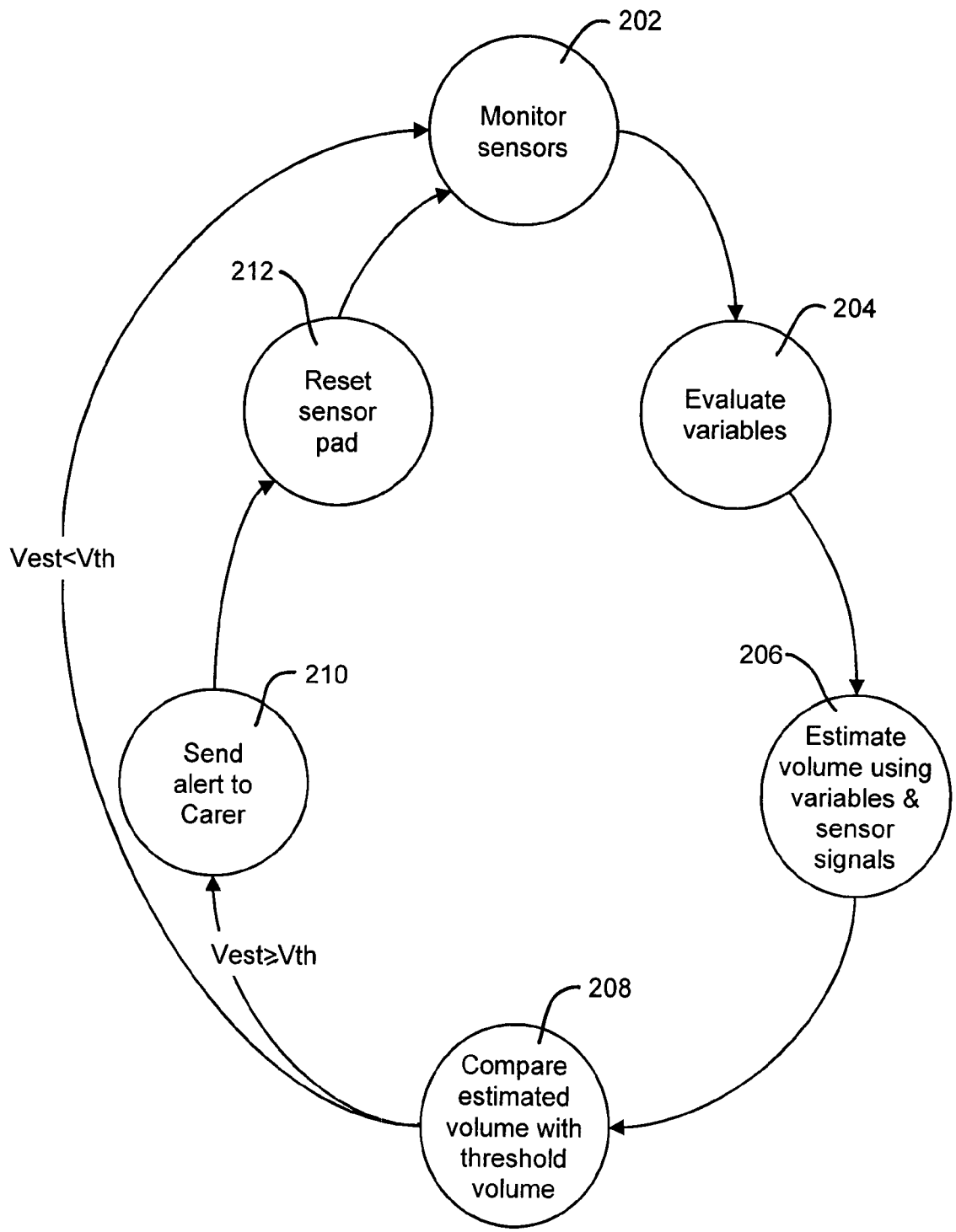
FIG. 2 is a flow diagram showing typical steps in using the monitoring system for continuous monitoring of patients for wetness, using a sensor.

The moisture monitoring system of the present invention can be used to monitor incontinence sufferers more efficiently than existing systems. FIG. 2 is a flow diagram illustrating typical steps involved in using the monitoring system for continuous monitoring of patients for wetness using sensors. In a step 202, the system monitors sensors applied to absorbent articles worn by patients in a care institution. If a sensor signal value exceeds an initial trigger value, in a step 204 the processor 106 (FIG. 1) derives variables from received sensor signals which, in a step 206 are used as inputs to an algorithm utilising a pre-determined mathematical model to estimate a volume of exudate in a wetness event. The mathematical model may be determined using any suitable statistical modelling technique such as regression analysis. In this example, the algorithm applies a mathematical model to estimate volume of exudate using the equation:

$$\text{Volume}=0.3\times(\text{Profile\_Area})+2.4\times(\text{Patient\_Weight})-0.6\times(\text{Patient\_Age}) \quad (Eq\ 1)$$

Profile_Area is the area under a curve of sensor signal versus time for a sensor element monitoring exudate conductivity. Eq 1 gives a confidence factor ($R^2$) of 0.63. It is to be understood, however, that Eq 1 is just one example of a mathematical model which may be used to characterise wetness events and that other models may be derived with also exhibit a satisfactory level of confidence.

In a step 208 the processor executes an algorithm to compare the estimated volume with a pre-defined threshold level. If the estimated volume is less than the threshold, the processor continues to monitor the sensor signals. If the estimated volume exceeds the threshold amount, then in a step 210 the processor sends an alert to a carer. Once a carer is alerted, the carer attends to the resident and may choose to change the absorbent article and in a step 212, the processor detects that the sensor has been disconnected from the system and resets the sensor data.

The threshold volume used by the processor to alert a carer may be a "qualifying amount" e.g. indicated as small, medium or large or a quantifying amount being a pre-defined volume e.g. 50 ml.

Preferably, the processor may also execute an algorithm to compare the estimated volume with a known estimated capacity of the diaper to give carers an indication of when the diaper is likely to become saturated with exudate so that it can be changed before a saturating wetness event occurs and the patient is made to feel uncomfortable by excess wetness.

The processor may also monitor the total amount of accumulated moisture in a series of wetness events in a single absorbent article and provide an indication to a carer as to when the absorbent capacity of the garment has been or is likely to be reached, to prompt the carer to change the garment for the patient's comfort and wellbeing.

Users may enter data, including patient specific demographic data such as gender, age, height and weight via user interface 108. As indicated in Equation 1 above, these data can also be utilised by the algorithm to estimate e.g. volume. Other entered data may include medical data, i.e. medication, amount of fluid and food intake, details of known conditions, recent surgeries, years in assisted care, years wearing an incontinence garment, continence function if known, and mental condition.

The processor 106 may be incorporated into a central monitoring station such as a nurse's station. The processor may also integrate with or be incorporated into existing nurse call and remote patient monitoring systems controlled at the nurse's station. The processor may also be integrated with other care management systems for streamlining access to non-sensor related data contained within other care management systems such as, for example, fluid and food intake, patient relocation, showering, toileting, surgeries etc.

User interface 108 may also include a transmitter which sends alerts to communication devices such as pagers or nurse phones carried by carers to indicate that there has been a wetness event, or that one is due to occur, or that physical inspection of the patient is required or due. In addition to the detection of wetness events which are estimated to exceed a threshold amount, these conditions warranting physical inspection may include when exudate is fecal in nature or when sensors detect blood, a parasite or a biological or chemical marker in the urine or faeces.

Figure 3:
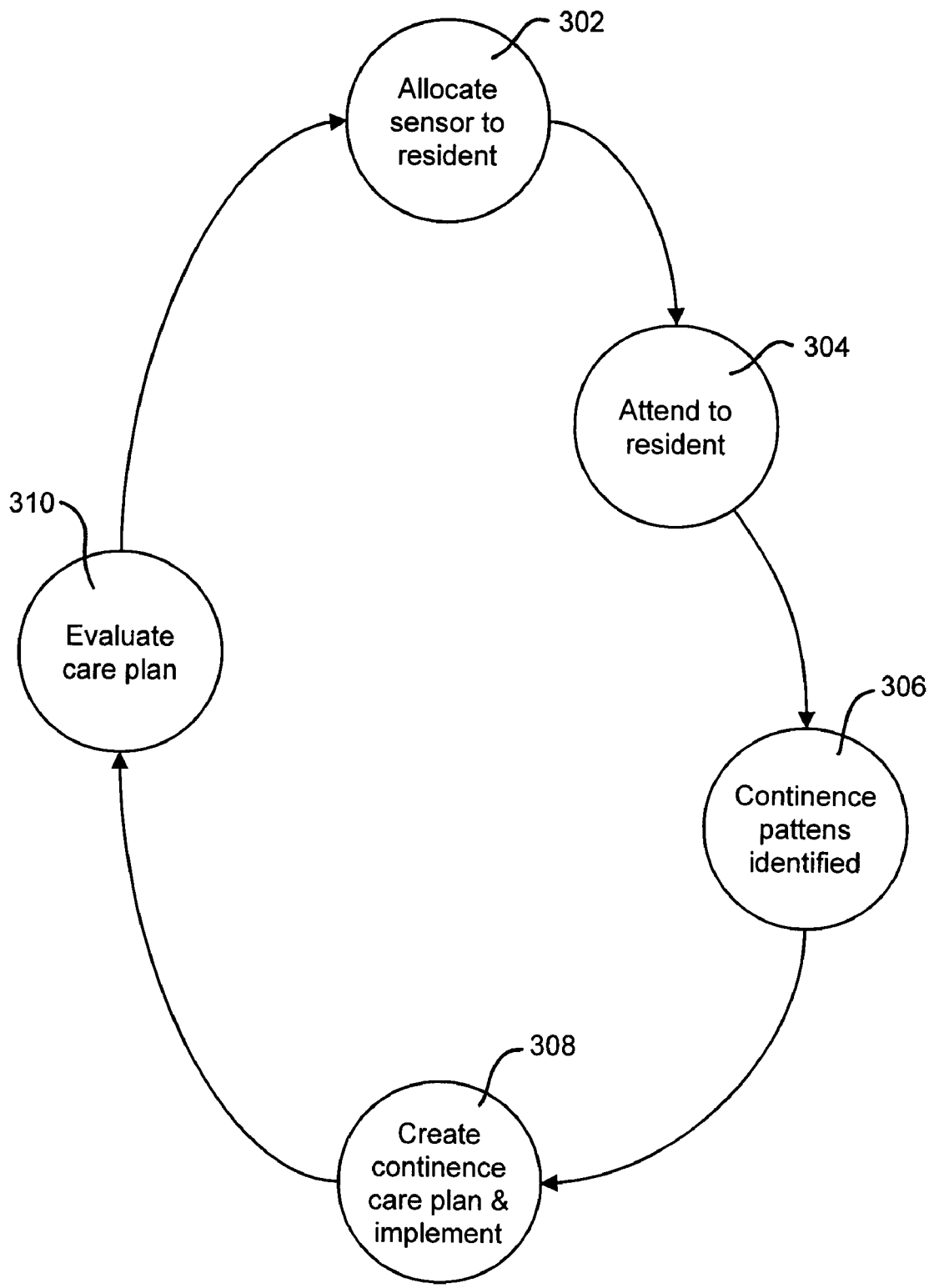
FIG. 3 is a flow diagram showing steps involving use of the invention for care planning.

FIG. 3 illustrates another use of the invention, where the moisture monitoring system is used in care planning to evaluate and plan the regularity and timing of a carer's manual checking of an individual's continence, and to schedule toileting. The care plan is based on an assessment performed using the monitoring system.

In a step 302, a sensor is allocated to a patient. The sensor has a transmitter unit attached and in a step 304 the patient is monitored for wetness for a continuous period of, for example, 3 to 5 days. During that period, the patient participates in usual activities and the patient is physically checked for wetness by a carer regularly, e.g. every hour. When a sensor signal received by the processor indicates a presence of exudate, an alert is sent to a carer who attends to the patient, changing the pad. Each time the carer checks or attends to the patient, observation data is recorded which includes the nature and amount of exudate (e.g. volume or mass obtained by weighing a soiled pad) and the time of observation.

In a step 306, observation data is used, along with a log of the sensor signals received at the input, to identify patterns in the patent's continence activity. In a step 308 the processor derives automatically, using an algorithm employing another mathematical model, a continence care plan based on the pattern, i.e. frequency and repetition of monitored events. The care plan includes a voiding or toileting schedule which statistically predicts wetness events based on the observed pattern. This is used by carers to plan the regularity (e.g. times of day) that a patient is to be manually checked for wetness and/or assisted with toileting and to plan when to empty the bladder or bowel, prior to periods in which a patient is known to have a pattern of incontinence events. Normal care of the patient can then take place without the need to continually monitor using a sensor.

The voiding schedule anticipates when a wetness event is statistically likely to occur and this can be used to automatically generate an audible and/or visible alert for a carer (e.g. presented on a screen of the user interface 108 or transmitted to a pager or the like) to attend to the patient by assisting with manual toileting or to change the patient's incontinence garment.

It is recommended that the toileting/voiding schedule is re-evaluated periodically (step 310) to maintain its accuracy, in keeping with changes in the patient's continence patterns. Re-evaluation may take place for example every 3, 6 or 12 months, or whenever actual wetness events do not correspond well with those anticipated by the voiding schedule.

In another use of the invention, the moisture monitoring system includes a log for recording wetness events detected by sensors including the volume, time and nature (urinary and/or fecal) of each event. These data are used to produce a bladder diary. These data may also be combined with details entered e.g. at the user interface 108 which relate to food and fluid intake (amount, kind and time), toileting and also any particular activities that the patient has undertaken.

The log may manifest in a memory device in communication or integrated with the processor. The processor may be located centrally and receive sensor signals relating indicative of wetness of a number of absorbent articles worn by different patients. Alternatively, there may be a pre-processor executing the algorithm located near the sensor, on the absorbent article. That is, the sensor and the part of the processor performing the analysis may be a provided together with the sensor. In such arrangement, the pre-processor may also incorporate a transmitter for transmitting data from the pre-processor to e.g. a central monitoring system which may include a display.

Figure 5A:
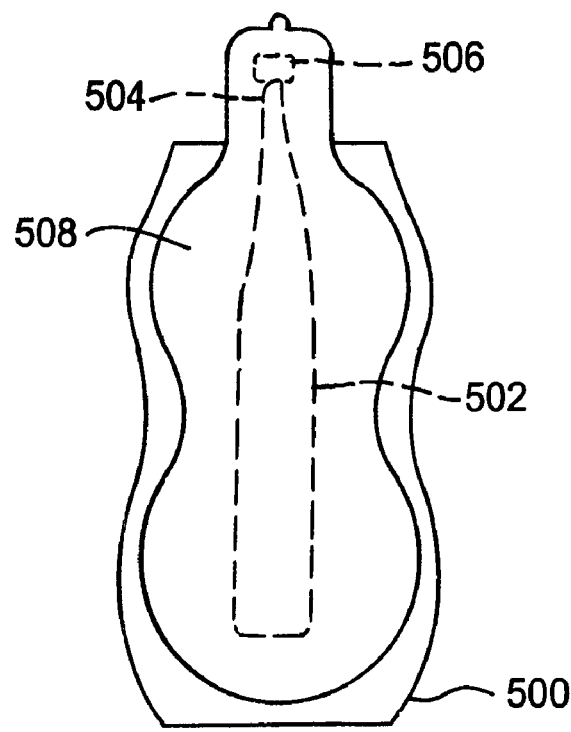
FIGS. 5a and 5b illustrate an example of a sensor used with an absorbent article, according to an embodiment of the present invention.
Figure 5B:
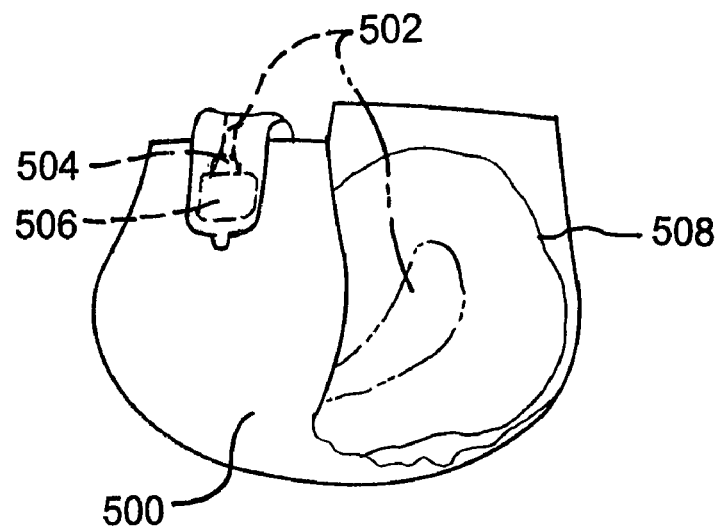

Referring now to FIGS. 5a and 5b, there is shown a schematic diagram of a sensor 502 according to an embodiment of the invention, applied to an absorbent article 500. The sensor 502 has a sensor element (shown in broken lines) which exhibits a change in conductivity when moisture is present, although other variables such as temperature could be used to detect moisture, as indicated in FIG. 6.

Figure 6:
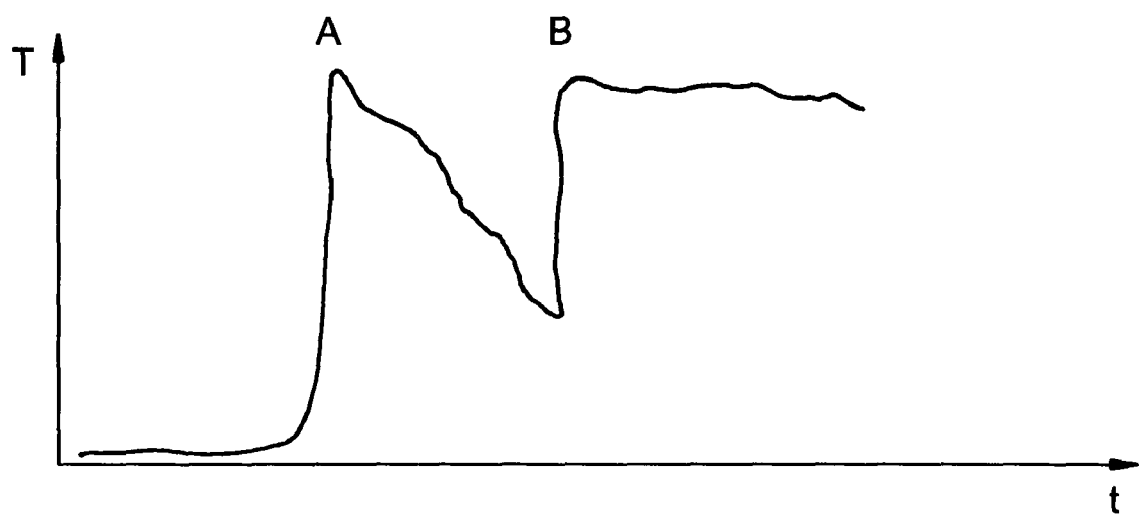
FIG. 6 represents a sensor signal showing temperature versus time.

FIG. 6 is a graph of temperature versus time. The rise in temperature at point A is indicative of a wetness event and the rate of decline indicates that the temperate moisture is being drawn away from the sensor element, into the absorbent article. The second leading edge peaking at point B indicates the occurrence of a second wetness event and the signal is sustained. This is typically indicative of a situation in which the absorbent article must be changed e.g. because of the size of the wetness event, because the article has reached its absorbent capacity, or a fecal event has occurred in which the exudate cannot be drawn into the absorbent layers of the article.

Returning to FIGS. 5a and 5b, an embodiment of the invention is shown in which the sensor elements 502 extend beyond a front edge of the absorbent article 500. In this arrangement, a connector 504 is also provided to which a signal receiver unit 506 may be attached. The signal receiver unit may consist of a storage component which records the time and magnitude of sensor signals. Alternatively/additionally, it may include a transmitter which conveys the time and magnitude of sensor signals to a remotely located processor. Alternatively/additionally, the signal receiver unit may include a pre-processor for executing an algorithm performing analysis of the sensor signals which are then stored locally for downloading and/or transmitted to a remote processor which conveys alerts to carers, formulates bladder diaries, voiding schedules or the like. In such arrangement, the signal receiver unit (i.e. pre-processor) may also include means for receiving data relating to a patient's toileting activities. The data may be received wirelessly via a contactless communication device, by a cable connection to an input device or other suitable means for example buttons or the like on the signal receiver unit itself, worn by the patient.

Preferably, signal receiver units 506 are re-useable, and are releasably connectable to the sensors via connectors 504. This connection may utilise any suitable connection means such as a male-female dual-in-line (DIL) connector or the like, as would be known to a person skilled in the relevant art. The signal receiver units may be attached to an absorbent article or to clothing worn by a patient in a manner which is comfortable for the patient to wear, and is also sufficiently robust to minimise the risk of damage or removal while in use. When the diaper/incontinence garment is changed, the signal receiver unit may be disconnected from the soiled sensor, cleaned and attached to a sensor on a new diaper/incontinence garment.

Alternatively, the signal receiver units and sensors may be disposable and incorporated into a diaper or absorbent article during manufacture. In this arrangement, the signal receiver unit may not be visible so the sensor may be activated by a switch or button which is felt through the layers of the diaper. Alternatively, a radio-frequency or other contactless system may be used to activate the device and/or transmit sensor signals to a central monitoring station. In a further alternative embodiment, all parts of the monitoring system are re-useable, although this may create hygiene problems and be undesirable for individuals left with the task of cleaning the components.

In the embodiments illustrated in FIGS. 5a and 5b, a cover layer 508 is provided over the sensor elements. In regions of the cover layer affected by exudate, it is preferred that the cover layer material is liquid permeable so that any moisture resulting from a wetness event can be drawn into the absorbent layers of garment 500. In a preferred embodiment, a flap or pouch is provided to contain the signal receiver unit (which may also provide a transmitting/pre-processing/memory functions). The flap or pouch may be provided by a portion 508a of the cover layer which extends beyond and folds over the front edge of the absorbent article and can be fastened in place by adhesive, Velcro® or other means. The flap or pouch deters individuals, particularly those with forms of dementia or mental illness from tampering with the unit. Preferably, the sensor and absorbent article are arranged in such a way that the signal receiver unit is attachable thereto outside the absorbent article.

The sensor and other components which are located on the diaper (e.g. transmitter, pre-processor) may be powered by a small battery or electronic component storing energy. Alternatively, the sensor may include or be part of an RFID or other passive device. To conserve power, the transmitter/pre-processor may deactivate when there has been no wetness event for a predetermined length of time. The devices may be reactivated when a wetness event occurs.

The processor analyses signals received from the sensors to characterise wetness events which are detected for each patient. Characterisation of wetness events by the processor may include characterising the cause of a wetness event by making a distinction between wetness resulting from incontinence, perspiration or other leakage or discharge which may occur due to bedsores or decubtious ulcers which can develop in immobile patients.

Figure 7:
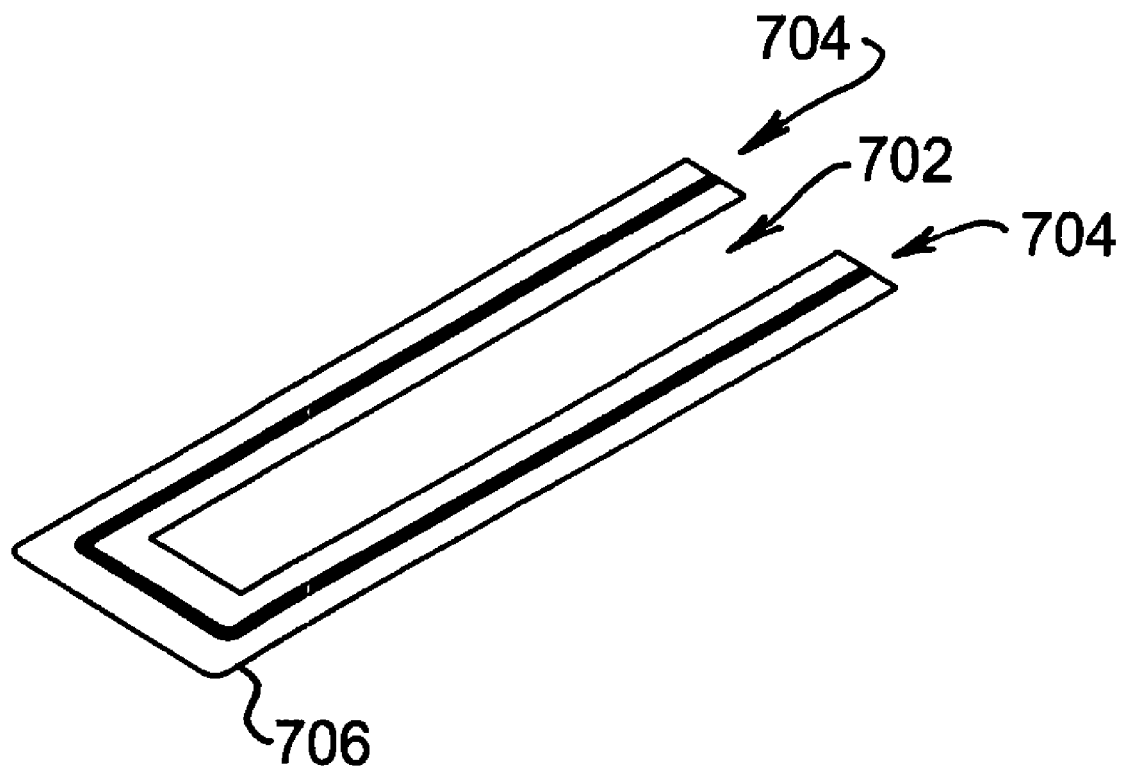
FIG. 7 illustrates an embodiment of a sensor having a channel between adjacent sensor elements.

A sensor 102 may be incorporated into a pad, diaper or adult incontinence garment when manufactured, or it may be provided separately and attached to an "off the shelf" diaper by way of adhesive or other fixation means. For the latter, sensor elements are provided on a substrate which may be liquid permeable so that exudate released by the wearer passes through the substrate (activating the sensor elements) and is drawn away from the user into the absorbent layers of the diaper. One or more pores and/or channels may be provided in the sensor substrate to facilitate drawing of exudate away from the skin surface into the diaper. FIG. 7 illustrates one such embodiment, where there is an elongate channel 702 provided between two elongate sensing elements 704 on a substrate 706 of a sensor. It may be desirable to use a sensor having a substrate of this kind with an absorbent article with super absorbent material correspondingly arranged in the article so as to draw fluid from the one or more channels in the sensor substrate into the absorbent layers and away from the wearer.

In one embodiment, sensors 102 are conductive elements. When an electrolyte such as urine contacts the conductive elements in sufficient quantity, a conductive bridge is formed between the elements and this can be detected by monitoring one or more electrical characteristics of the elements such as resistance or conductance, capacitance or the like. The conductive elements may be formed using any suitable conductive materials or combinations of materials including gold, copper, silver, conductive inks, polymers, tapes, resins and threads, other suitable conductive polymeric materials, conductive film, fibres or electrodes including, for example, an inert metal. Alternatively/additionally, the sensor elements may detect changes in temperature, pH odour, gas, or the presence of blood or a chemical or biological marker in exudate to indicate a presence of moisture.

Production of the sensor may utilise a range of manufacturing methodologies. One example is screen printing or etching which can be employed to deposit the sensing elements on a suitable substrate. In one form, the sensor may be provided in the form of a flexible printed circuit board formed on a Mylar or other suitable flexible substrate. For three-dimensional arrays, the sensor elements may be deposited on a number of substrate layers which are then bonded into a multilayer liner. For sensor elements incorporated into diapers, depositing the layers on the various absorbent layers of the diaper can be integrated into the diaper manufacturing process.

The sensor elements may be elongate or provided in the form of grids, dots or the like, arranged in a pattern along and/or in the diaper or a pad or liner attachable thereto. By utilising, for example, screen printing or etching techniques, effective patterns can be designed and printed in layers of the sensor quickly and accurately. Advantageously, screen printing can deposit conductive polymers, inks and the like in very fine lines or grids between which exudate including urine and faeces may be absorbed into deeper, more absorbent layers. This enables conductive elements of a sensor to be incorporated into a diaper or absorbent article without significantly affecting the performance of the diaper.

Figure 8:
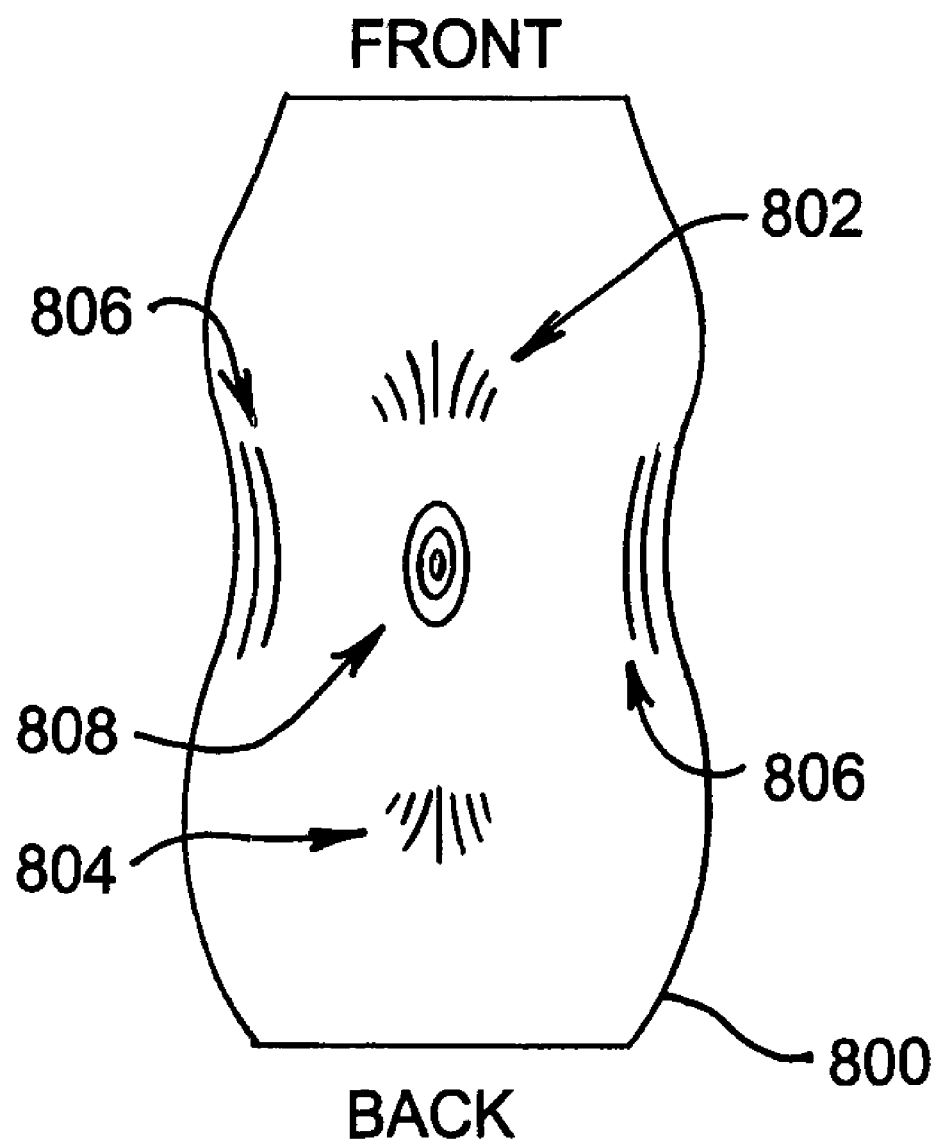
FIG. 8 is a schematic illustration of a diaper or adult incontinence garment showing a pattern of sensor elements according to an embodiment of the invention.

The sensor elements are preferably provided in a quantity and pattern sufficient to enable detection of moisture in different locations in an absorbent article being worn by a user. The pattern may be a two-dimensional pattern in which sensor elements are provided in a single layer or in a three-dimensional pattern. The pattern of sensor elements is preferably such that the elements are focussed in regions of the article where there is a greater likelihood of them being affected by a wetness event. FIG. 8 is a schematic drawing of a diaper 800 laid flat, showing one example of a pattern of sensor elements which may be suitable. Each of the sensor elements may be uniquely identified enabling sensor signals to convey to the processor data indicating that wetness is present, as well as the location of the sensor element(s) detecting the wetness. This enables the processor to determine where in the absorbent article and the extent to which the wetness has occurred. Spread of wetness may also be identified.

In one embodiment, the sensor has a plurality of layers and the sensor elements are arranged in a three-dimensional pattern within the layers. A three-dimensional array is advantageous for a number of reasons. Firstly, absorbent articles such as diapers are flexible in nature and therefore prone to folding or scrunching particularly in regions around the legs. To circumvent a problem in which 2 or more conductive elements of a sensor are caused to "short" together as a result of a fold in the article or movement of a wearer, adjacent conductive elements may be placed in alternate layers of the sensor, separated by an electrically insulating permeable layer to prevent shorting in the absence of wetness.

Secondly, by positioning sensor elements in different layers, it is possible for the sensor to convey additional location data to the processor relating to the depth at which moisture is detected. This is particularly important for sophisticated diapers and incontinence garments which are multi-layered in their construction and designed with super absorbent and "wicking" properties to draw wetness away from the wearer and direct it to chambers or zones in the absorbent layers where it is retained. Positioning sensor elements in or near various absorbent layers of the article can convey further relevant data to the processor which may relate to, for example, the degree of wetness (or fullness) of a storage chamber within a diaper. Also, elements located at various depths allow the system to monitor the absorption of fluid into a diaper. Thus, the sensor will not require 'pooling' of moisture to detect wetness. This is especially useful in view of the fact that most modern absorbent garments are manufactured to maximise the absorption of liquid away from the skin.

As indicated above, the sensor elements are arranged in a pattern which maximises the ability to detect relevant data, for use in characterising wetness events. For example, as illustrated in FIG. 8, the pattern may provide sensor elements more densely in a region toward the front of the absorbent article (802), to the rear of the absorbent article (804), and around the leg openings (806) and in the centre, between the leg opening (808), where liquid is likely to drain. Positioning the sensor elements in this way improves the detection of urinary wetness which normally occurs toward the front of an absorbent article, detection of faecal wetness which normally occurs to the rear of an article, and detection of wetness resulting from perspiration which can frequently occur, for example, toward the sides in the crotch area near the crease of the wearer's legs, and toward the middle of the diaper.

The sensor may also provide means to detect temperature, pressure, presence of a gas or odour in the absorbent article and/or the presence of a biological or chemical marker indicating presence of bacteria, sugar, parasites or the like in the urine or faeces. This is particularly useful for patients who lack the ability to control where and/or when a voiding event will occur. Data pertaining to these further parameters can also be used, in combination with signals from the conductive elements to further characterise a wetness event, provide a diagnostic indicator, or at least give a carer an early indication that a particular patient is in need of further attention. Other sensor elements may also be incorporated to indicate whether the patient is moving or in a sitting. Lying or standing position.

The sensor signals may be logged regularly, say, every 100 milliseconds or sufficiently frequently to reliably and accurately detect and distinguish an event. Signals received by the processor can reveal data indicating for example (i) detection of wetness and (i) location of the detected wetness. These signals can vary over time, as liquid is absorbed though the diaper and further wetness events occur. By monitoring these signals in time, it is possible for the processor to derive further useful parameters such as volume of exudate in an event and total volume absorbed, using mathematical modelling.

Also, the volume of exudate released can be computed using such factors as the distance between sensor elements detecting the wetness, the rate of transfer of moisture between these elements and the absorption properties of the materials used. These materials may include polymer fibres, natural fibres, gels, textiles, fabrics, papers or a combination of these materials.

The processor may also be programmed with or can interrogate a database of "event signatures" or models characterising certain wetness events and correlate the sensor signals with the event signatures/models to characterise wetness events which are detected. The models may be embodied in any form including mathematical models as described above, graphs or look up tables.

Advantageously, by including laterally placed sensor elements in the sensor pattern, incontinence events can be detected irrespective of whether the patient is in the sitting, lying or standing position. For instance, if the patient is lying on his side, laterally located sensor elements are more likely to detect urinary exudate than the frontal elements which would be activated if the patient was standing or sitting.

Lingering wetness may be indicated by failure of the signal to recover to a normal level. A prolonged high sensor signal value may indicate the presence of faecal matter which, unlike urine, may not be drawn into the absorbent layers of the diaper but remains in contact with the sensor elements. Detection of a faecal event should be accompanied by an alert to a carer to change the diaper so as to avoid prolonged wetness and discomfort. A lingering wetness may also be indicative of a full diaper, resulting from inability of the diaper to draw any more urine away from the wearer. This condition should also be communicated to a carer.

The system of the present invention may be utilised with a diaper to be worn by the patient, which diaper has features which enable it to monitor incontinence, particularly urinary incontinence, by, for example, collecting data from the patient wearing the diaper, and transmitting it to a location where such data may be processed. The diaper may also include features which enable samples of, for example, urine, to be withdrawn in situ from such a diaper, for testing.

Figure 9:
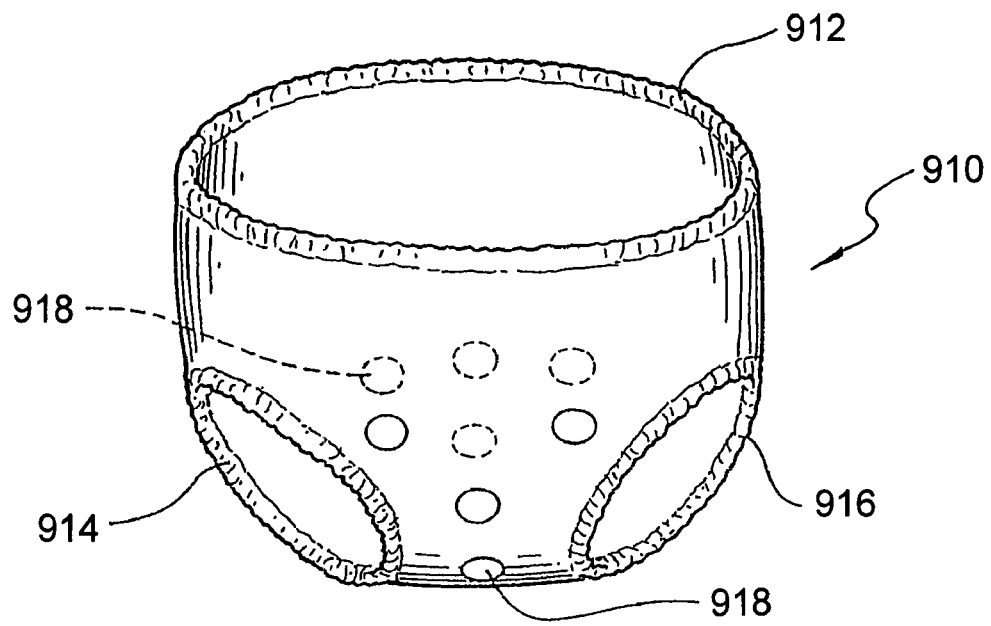
FIG. 9 is a diagrammatic perspective view of a diaper in accordance with one embodiment of the present invention.

FIG. 9 shows a diaper 910 which is adapted to be worn by a patient (not shown). Preferably, the diaper 910 is disposable and/or re-usable, and may have an elasticised waistband 912 and elasticised upper thigh bands 914, 916. The diaper 910 is intended to permit the estimation of the volume of urine flowing from the patient in real time. This is effected by the placing of one or more moisture (wetness) sensors 918 at different locations in the diaper 910. The sensors 918 may form part of a radio transmitting and data capturing arrangement (not shown), such as the one described above.

The sensors 918 may constituted by conductive inks or other means adapted to detect the presence of moisture. The sensors 918, are connected to the aforementioned arrangement, which may be a purpose designed continence management system which captures the data captured by the sensors 918, which data is recorded via e.g. radio transmission or the like to the processor described above. Some of the data may also be transmitted to nursing staff or a nursing station responsible for the management of the incontinence episode in an appropriate manner for the patient or resident in question.

The conductive inks used in the sensors 918 are preferably based on low-cost materials such as carbon, formulated on the carbon content of different concentrations and composition, to achieve the most appropriate sensitivity for moisture detection. Prior art conductive units are silver-based, and accordingly are typically too expensive for use in a disposable diaper.

The choice of carbon or a similar inert substance will reduce the likelihood of interference with chemical markers, which may be incorporated into the sensors 918, for the detection of clinically relevant substances of the type referred to earlier in this specification. Information captured by the chemical markers may be processed for improved management of clinical conditions of residents and patients by medical or nursing staff.

Preferably, the conductive ink will be such that rapid drying or curing will be achieved to enable manufacture of disposable diapers 910 to be carried out at rates consistent with the production of existing and future diapers, presently in the order of 400 diapers per second. The manufacturing process may be carried out using ultraviolet light in a manner similar to that used in rapid curing of dental materials for various dental procedures such as dental fillings.

In a preferred arrangement, the volume of urine passed by the resident or patient, preferably in a unit of time, will be established using a mathematical model computed by using such factors as the distance between sensors 918, the rate of transfer of moisture between sensors 918, and the absorption properties of the materials used, such as polymer fibres, natural fibres and combinations of polymer fibres and natural fibres.

Figure 10:
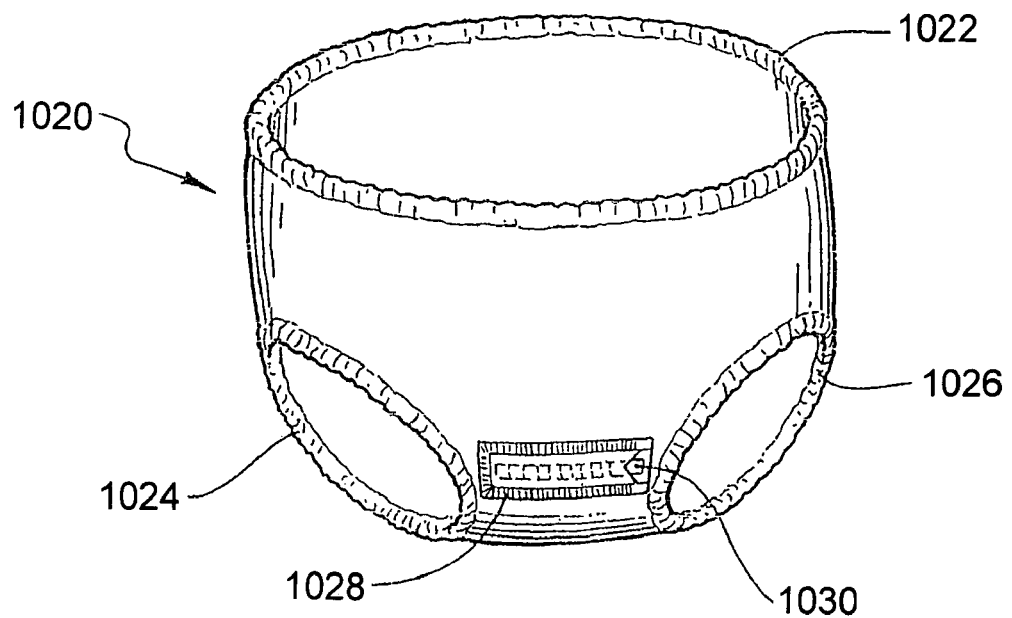
FIG. 10 is a diagrammatic perspective view of a diaper in accordance with a second embodiment of the present invention.

Turning now to FIG. 10, a diaper or the like 1020 which may fundamentally be similar to the diaper 910 of FIG. 9, and which is adapted to be worn by a patient or resident suffering from some form of incontinence. Preferably, the diaper 1020 is disposable and/or re-usable, and preferably has an elasticised waistband 1022 and elasticised upper thigh bands 1024, 1026.

The diaper 1020 has a sleeve 1028 located preferably in the area of the diaper 1020 close to the pubic area of the patient or resident. The sleeve 1028 is intended to house a diagnostic strip or the like 1030. Such diagnostic strips 1030 may be of the Multistix/Combistix type or similar to other strips which are able to detect relevant substances in urine, for example blood, sugar, nitrites, leucocytes, urea, specific gravity, protein, and other substances. As some of the chemical sensors on the strips 1030 use and are derived from blood products, the sleeve 1028 will protect the skin of the wearer from such blood derived products and thus accidental infection with hepatitis B, hepatitis C or HIV.

It is considered that as the information to be obtained from the diagnostic strips 1030 may need to be obtained within certain time frames, the sleeve 1028 will need to allow for a sufficient volume of urine to be captured so that the urine may make contact with the strip 1030, and for radio transmission of data to take place within the required time frame.

Figure 11A:
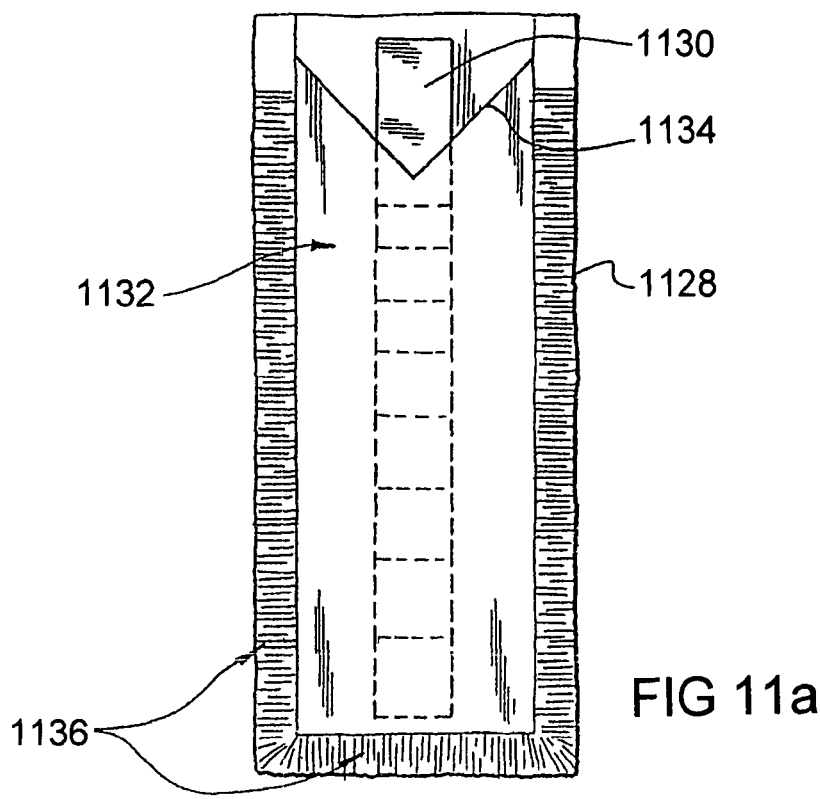
FIG. 11a is a front elevation of an embodiment of a sleeve for a diagnostic strip.
Figure 11B:
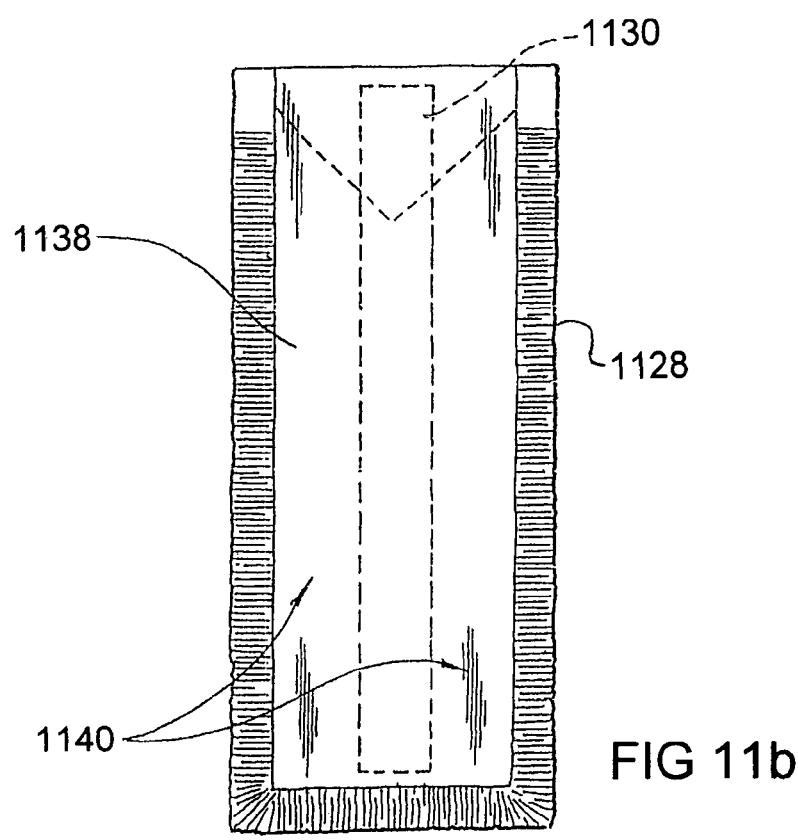
FIG. 11b is a rear elevation of an embodiment of a sleeve for a diagnostic strip.

FIGS. 11*a* and 11*b* show front and rear views of an exemplary sleeve 1128 for a diagnostic strip 1130. The sleeve 1128 is secured to diaper 920, 1020 as will be described hereinafter, and is designed and constructed of materials which will attract and capture urine from the patient or resident. This will expose the chemical sensors on the strip 1130 to the collected urine.

The front 1132 of the sleeve 1128 may be provided with a V-shaped notch 1134 for ease of insertion of a diagnostic strip 1130. Pores and channels 1136 may be provided to facilitate the drawing in of the urine to the interior of the sleeve 1128, effectively "sucking up" the urine. The rear 1138 of the sleeve 1128 may be provided with adhesive material 1140 for attaching the sleeve 1128 to the diaper 1120 or pad, in much the same manner as used in feminine hygiene products.

A sleeve 1128 will allow urine to be captured in sufficient volume to permit the detection of relevant clinical substances. The interpretation of the results of such detection are preferably based upon a recalibration of what may be regarded as normal or abnormal, compared to existing "dipsticks", which have established normal and abnormal values for interpretation. This re-standardising may be required to take account of any alteration which may occur in the components in the urine samples, as a result of the present invention. For example, diaper fibres may trap some white blood cells, so that a new "normal value" may be needed to be established to cater for such a possibility. As a consequence, a new lower value for the number of leucocytes in a sample may be required.

Another example relates to the test for the albumen:creatinine ratio in a spot urine sample. A level of 0.7 mg/mmol corresponding to a urinary excretion rate of more than 5 mgm/min would indicate a high-risk (in cardiovascular terms) patient requiring aggressive treatment. This marker of arterial damage may be considered with raised cholesterol and hypertension as a serious risk factor for cardiovascular disease. Such values would be revised if necessary for the purposes of the present invention.

The sleeve operates as follows. Urine is drawn into the sleeve 1128 via capillary action, osmosis and semipermeable membrane processes, thereby bringing the urine into contact with a diagnostic strip 1130, which may be a proprietary strip such as marketed under the Bayer and Roche brands, to enable the "reading" to take place in a timely fashion. The carer or nurse will have been alerted to the availability of the urine sample through the radio-based system and software-based system described earlier in this specification.

Patients or residents may be required to take standard known quantities of substances such as creatinine to carry out reliable, accurate tests which the incontinence management system is able to interpret reliably. Such ingested substances may be excreted in an unmetabolised form, for example, as creatinine asparginine, or may be actively metabolised and measured as a metabolite in the urine.

Figure 12:
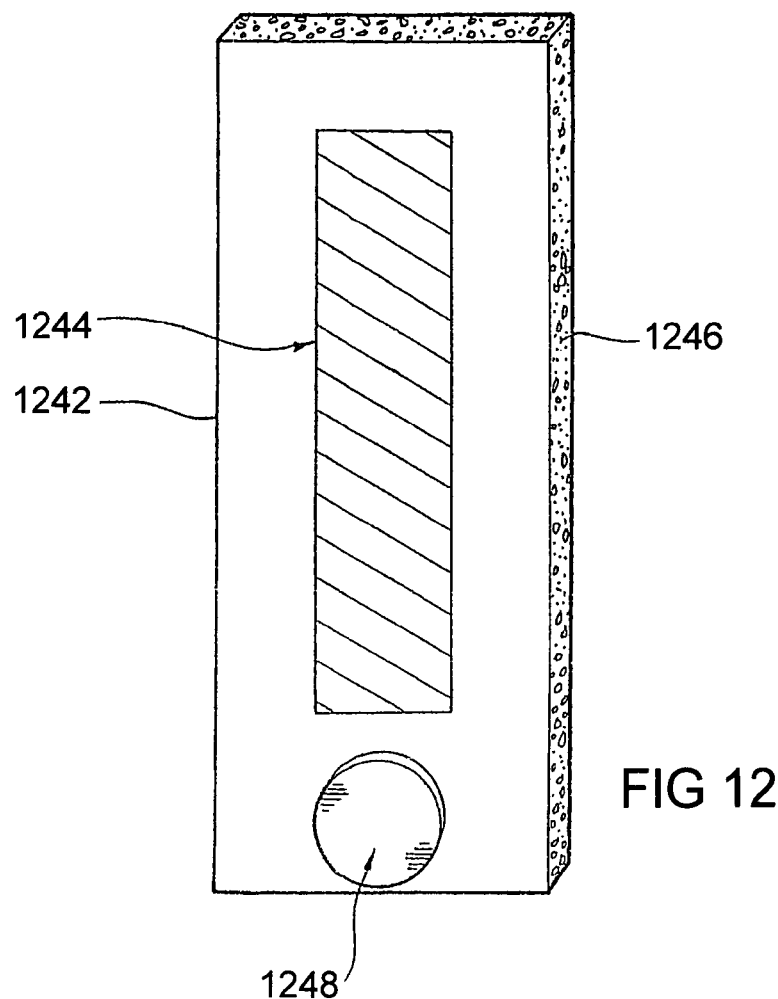
FIG. 12 is a diagrammatic perspective view of a pad for use in a diaper.
Figure 13:
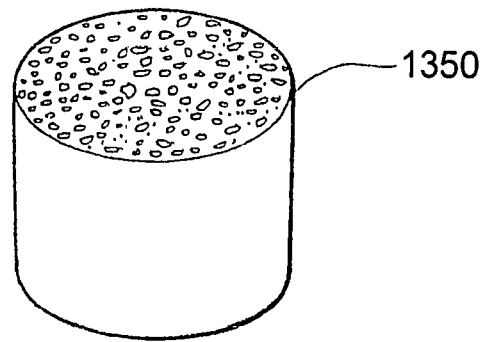
FIG. 13 is a diagrammatic perspective view of an alternative pad for use in a diaper.

The embodiment of FIGS. 12 and 13 of the present invention makes possible the interpretations of findings in near real time, as the requirement of testing fresh, recently passed, urine is essential for the most accurate interpretations to take place.

In FIG. 12 there is shown a pad 1242 which preferably is adapted to be attached to a diaper (not shown) of a neonate, baby or a child, more preferably by adhesive means such as 1244. The pad 1242 itself is preferably formed from an absorbent material 1246 such as a sponge or sponge-like material e.g. containing super absorbent particles, to take up urine excreted by the baby. The pad 1242 may also preferably be fitted with a transmitter 1248 for transmitting data to the system(s) described previously in this specification. One example of such a signal would be a signal representative of the fact that voiding had taken place. This may be accomplished by linking the transmitter 1248 with a wetness sensor (not shown).

Currently, there are three existing sample collection methods, where the collection samples are carried out by "catch" techniques, adhesive collection bags, or suprapubic bladder puncture. There are also "time interval" tests, such as 1-hour and 2-hour tests to establish levels of incontinence during the stated time intervals, in which conventional pads are simply weighed to determine the volume of urine. These are termed "pad tests".

The pad 1242 shown in FIG. 12 is much more sophisticated. It preferably comes in three versions. The first version would be a "wetness only" signalling pad, where a parent or nurse would be alerted in real time of passage of urine, would collect the pad and place it in a suitable container to be sent promptly to the microbiology and pathology lab for testing, or would draw up the urine via a syringe for placement in a container, with the container being sent to the lab.

The second type involves the pad 1242 having a collecting chamber (not shown) incorporated therein, into which urine has been drawn. This chamber is preferably removable, so that it may be removed when a predetermined amount of urine, or urine passed in a predetermined period of time has been passed, and sent to the microbial/pathology lab.

The third type of pad 1242 would have a chamber such as that described in relation to the second type, but which would include diagnostic strips of the type and purpose described hereinbefore in relation to FIGS. 9 to 11*b*. The design of the collection chamber, sleeve or pocket will be such that it will collect urine for dipstick testing, for collection of samples to be transported for pathology/bacteriology testing, or in situ testing using the new sensors designed for the incontinence management system.

The collection chamber, sleeve or pocket will be designed in conjunction with the diaper to which it is attached, which diaper draws and feeds the urine into the chamber, to maximise the volume of urine collected, when only small voids have occurred.

Alternatively, urine may be expunged form a urine-soaked pad 1242 via a special container which may expel urine by the use of a plunger (not shown), which may be compared to the plunger in a coffee plunger, which is able to force urine into a sealed compartment (not shown), separate from the pad 1242.

The pad 1242 may have capillary channels (not shown, but preferably similar to channels 1136 of FIG. 11*a*, to draw the urine towards the collection chamber. The pad 1242 and/or diaper containing the pad 1242 may also preferably use materials designed for osmosis, capillary action or other manner of providing directional flow of urine to assist in the transfer of the urine to a location where it is required. FIG. 13 shows an alternative pad 1350, which may be generally similar to pad 1242 of FIG. 12, but which has a generally cylindrical shape.

Reference is now made to the extension of the present invention to other bodily fluids and exudates from the body of a person. In the case, for example, of serous and other exudates, a dressing for a wound are preferably provided such that information about the would may be relayed via sensors located on or in association with the dressing, which would otherwise be difficult to determined because conventional dressings or casts would be in the way.

It may also be the intention of the present invention to provide sensors of the dipstick and/or electronic type for dressings on wounds. Additional components, ions and chemical markers of bodily fluids or exudates from the body, may be detected in situ or via the sensors located on or in association with the sensors. Presently, such body products are tested away from the patient in biochemical and bacteriological laboratories. The sensor-equipped dressings may also be used to inform nursing staff of ooze, and content.

It is to be understood that various modifications, additions and/or alterations may be made to the parts previously described without departing from the ambit of the present invention as defined in the claims appended hereto.

The invention claimed is:

1. A moisture monitoring system for monitoring wetness in one or more absorbent articles, the system including:
   an input for receiving one or more sensor signals indicative of a presence of wetness in an absorbent article;
   a processor; and
   user interface for communicating with a user of the system;
   wherein the processor executes an algorithm to analyze the one or more sensor signals by applying the one or more received sensor signals to a pre-determined mathematical model to characterize a wetness event in an absorbent article; and
   wherein the system has devised the pre-determined mathematical model using sensor signal data previously received by the system, the mathematical model representing a relationship between one or more variables obtainable from the received sensor signals and a characteristic used to characterise a wetness event.

2. A moisture monitoring system according to claim 1 wherein the processor executes the algorithm to characterise a wetness event in an absorbent article by determining one or more of:
   (i) an estimated volume of exudate in a wetness event; and
   (ii) the nature of exudate in a wetness event.

3. A moisture monitoring system according to claim 1 wherein the system uses the received sensor signals and/or variables derived from the received sensor signals to derive one or more parameters suitable for use in the mathematical model.

4. A moisture monitoring system according to claim 3 wherein the system applies variables derived from the one or more received sensor signals to optimize the mathematical model for characterizing a wetness event.

5. A moisture monitoring system according to claim 1 wherein the one or more sensor signals are indicative of one or more of:
   (i) conductivity of the exudate;
   (ii) temperature of the exudate;
   (iii) location of the exudate;
   (iv) pH of the exudate;
   (v) pressure within the absorbent article;
   (vi) odour within the absorbent article;
   (vii) presence of a gas in the absorbent article;
   (viii) presence of blood and/or a biological marker and/or a chemical marker in the exudate.

6. A moisture monitoring system according to claim 1 wherein variables derived from the sensor signals are selected from the group including:
   (i) area under a sensor signal curve;
   (ii) highest sensor signal value in a predetermined time period;
   (iii) maximum value of a leading edge of the sensor signal;
   (iv) rate of decay of sensor signal after a leading edge;
   (v) a volume estimated in a previous wetness event;
   (vi) time of onset of a wetness event;
   (vii) time of termination of a wetness event; and
   (viii) duration of a wetness event;
   (ix) time of day of a wetness event; and
   (x) time elapsed since last wetness event.

7. A moisture monitoring system according to claim 1 wherein the processor is configured to determine one or more of:
   (a) a likelihood of an imminent wetness event;
   (b) an estimate of when a wetness event is likely to occur;
   (c) an estimate of a degree of fullness of an absorbent article; and
   (d) an estimate of when an absorbent article is likely to reach its absorbent capacity.

8. A moisture monitoring system according to claim 1, wherein the user interface includes a wireless transmitter configured to transmit a signal to a user of the system to indicate that a predetermined volume of wetness has been detected in an absorbent article.

9. A moisture monitoring system according to claim 1 wherein the system is configurable to provide a toileting or voiding diary.

10. A moisture monitoring system according to claim 1 wherein the system is configurable to derive a toileting or voiding schedule for an individual, based on wetness events monitored using the monitoring system.

11. A moisture monitoring system according to claim 10 wherein the system is configured to predict, based on a derived toileting or voiding schedule, when an individual is likely to experience a wetness event which meets pre-defined criteria for manual checking.

12. A moisture monitoring system according to claim 1 wherein the system is further adapted to communicate automatically, an alert to a carer when one or more pre-defined criteria for manual checking are satisfied.

13. A moisture monitoring system according to claim 1 wherein the system is configured to classify a possible form of incontinence suffered by a patient monitored by the system, the form of incontinence being selected from the group including urinary, fecal, dribble, stress, overflow, urge, mixed urinary (MUI), total and functional incontinence.

14. A moisture monitoring system according to claim 1 wherein the system is configured to perform one of recognizing and predicting the occurrence of lingering wetness in a region of an absorbent article.

15. A moisture monitoring system according to claim 1 wherein the processor is affixable to a sensor, an absorbent article or to a garment worn by a wearer of an absorbent article.

16. A moisture monitoring system according to claim 1 wherein the processor is incorporated into a central monitoring station adapted to receive sensor signals from a plurality of sensors associated with one or more absorbent articles.

17. A moisture monitoring system according claim 1 wherein the processor includes a pre-processor associated with a sensor of an absorbent article.

18. A moisture monitoring system according to claim 2, adapted to reconfigure the mathematical model for use with one or more of a particular individual being monitored, a different sensor type and a different absorbent article type, by:
for a training period using the particular individual, the different sensor type or the different absorbent article type, monitoring wetness at regular intervals by obtaining sensor signals and obtaining observation data; and
reconfiguring the mathematical model so that there is satisfactory correlation between wetness estimates produced using the sensor signals and the reconfigured mathematical model, and wetness observations from the observation data obtained during the training period.

19. A moisture monitoring system according to claim 18 wherein reconfiguring a mathematical model involves determining one or more new parameters for the mathematical model.

20. A moisture monitoring system according to claim 18 wherein reconfiguring a mathematical model involves application of a linear regression algorithm.

21. A moisture monitoring system according to claim 18 wherein the observation data includes measurements indicating an amount of wetness in the absorbent article and time of measurement.

22. A moisture monitoring system according to claim 18 wherein the observation data includes one or more of:
demographic information; and
patient information.

23. A moisture monitoring system according to claim 1 further including one or more sensors for use with an absorbent article being monitored for wetness, the sensor including a plurality of sensor elements arranged in a pattern which provides an improved ability to detect wetness.

24. A moisture monitoring system according to claim 23 wherein the sensor elements are arranged in a pattern in which there are more sensor elements in regions having higher propensity for variable moisture or temperature.

25. A moisture monitoring system according to claim 23 wherein, when applied to or incorporated into an absorbent article, one or more sensor elements extend beyond an edge thereof.

26. A moisture monitoring system according to claim 25 wherein, when applied to or incorporated into an absorbent article, one or more sensor elements extend beyond a front edge thereof.

27. A moisture monitoring system according to claim 23 further including, for each absorbent article being monitored, a signal receiver unit and a connector for connecting sensor elements associated with an absorbent article to an associated signal receiver unit.

28. A moisture monitoring system according to claim 23 further including, for each absorbent article being monitored, a cover layer over the sensor elements, the cover layer extending beyond an edge of the absorbent article and including means for enclosing a signal receiver unit attachable to one or more of the sensor elements.

29. A moisture monitoring system according to claim 23 wherein, when applied to or incorporated into an absorbent article, one or more sensor elements are arranged for connection to a signal receiver unit outside the absorbent article.

30. A moisture monitoring system according to claim 27 wherein the signal receiver unit includes storage means for storing sensor signals collected over a period of time.

31. A moisture monitoring system according to claim 27 wherein the signal receiver unit includes means for receiving data relating to a patient's toileting activities.

32. A moisture monitoring system according to claim 23 wherein the pattern includes sensor elements positioned toward the sides of the absorbent article, near an opening for receiving a leg of the wearer.

33. A moisture monitoring system according claim 23 wherein the pattern includes sensor elements located at two or more depths of the absorbent article.

34. A moisture monitoring system according to claim 23 wherein the sensor includes a sensor substrate, the sensor substrate having one or more channels arranged between adjacent elements of the sensor.

35. A moisture monitoring system according to claim 34 for use with an absorbent article having super absorbent material arranged in the article so as to draw fluid from the one or more channels in the sensor substrate.

36. A moisture monitoring system according to claim 23 wherein the sensor is provided on a flexible substrate affixable, by adhesive or other means, to an absorbent article wearable by a user.

37. A moisture monitoring system according to claim 23 wherein the sensor elements detect wetness at various identifiable locations with respect to the absorbent article, the locations selected from the group including:
(a) toward the front of the absorbent article;
(b) toward the rear of the absorbent article;
(c) toward a side of the absorbent article; and
(d) substantially centrally of the absorbent article.

38. A moisture monitoring system according to claim 23 wherein the pattern of sensor elements facilitates improved detection of moisture from a user in a range of positions including standing, sitting, lying prone, lying supine and lying on the side.

39. A moisture monitoring system according to claim 23 wherein the sensor elements are arranged to detect spread of moisture from a wetness event in two or more directions.

40. A moisture monitoring system according to claim 23 wherein the sensor pattern includes one or more of:
elongate sensor elements;
sensor elements arranged in a grid; and
an array of sensor element dots.

41. A moisture monitoring system according to claim 23 wherein the sensor includes sensor elements for detecting one or more of electrical conductivity, temperature, pressure, pH, odour, gas and presence of a biological or chemical marker in exudate and location of exudate.

42. A diaper for a person to wear, for use with the moisture monitoring system of claim 1 wherein said diaper includes a sleeve for the insertion of a diagnostic strip.

43. A diaper according to claim 42 characterised in that said sleeve is located on said diaper close to, in use, the pubic area of a wearer.

44. A diaper according to claim 42, characterised in that said diaper has means designed to direct fluids excreted by said person, to said sleeve.

45. A diaper according to claim 42, characterised in that said sleeve is provided with a V-shaped notch to facilitate the insertion of a diagnostic strip.

46. A diaper according to claim 42, characterised in that said sleeve is attachable to said diaper by adhesive material.

47. A diaper according to claim 44, characterised in that said means designed to direct fluids excreted by said person, to said sleeve, is constituted by pores and/or channels.

48. A diaper according to claim 47, characterised in that said pores and/or channels are located around the periphery of said sleeve.

49. A diaper according to claim 42, characterised in that sleeve is adapted to retain a predetermined amount of exudate to facilitate contact of said exudate with said strip.

50. A diaper for a person to wear, for use with the moisture monitoring system of claim 1 wherein said diaper is provided with a plurality of sensors at different locations in said diaper.

51. A diaper according to claim 50, characterised in that said sensors are wetness sensors.

52. A diaper according to claim 51, characterised in that said sensors are adapted to permit the estimation of the volume of exudate flowing from the patient in real time.

53. A diaper according to claim 52, characterised in that the volume of exudate passed by the person wearing said diaper, preferably in a unit of time, is established using the mathematical model and computed by using such factors as the distance between said sensors, the rate of transfer of moisture between said sensors, and the absorption properties of the materials used, such as polymer fibres, natural fibres and combinations of polymer fibres and natural fibres.

54. A diaper according to claim 53, characterised in that data from said sensors is transmitted using radio technology, and in that said data is processed using software running the aforementioned mathematical model.

55. A diaper according to claim 50, characterised in that each of said sensors is constituted by conductive inks.

56. A diaper according to claim 50, characterised in that the spacing of said sensors is at different thicknesses in material forming at least a part of said diaper.

57. A pad for use with a diaper, and the moisture monitoring system of claim 1, wherein said pad is associated with transmitting means, for transmitting signals representative of an aspect of fluids absorbed by said pad, to a remote location.

58. A diaper according to claim 57, characterised in that said pad includes a chamber for collection of said fluids.

59. A diaper according to claim 58, characterised in that said chamber is removable.

60. A moisture monitoring system according to claim 1 configurable to adapt a mathematical model to characterise a wetness event in an absorbent article being monitored using one or more of a new sensor type, new sensor element and a new type of absorbent article not previously used with the moisture monitoring system.

61. A moisture monitoring system according to claim 1 wherein the processor is configured to receive automatically data pertaining to known features of an absorbent article selected from a group including: volume capacity, type, brand and location of sensors embedded therein.

* * * * *